(12) United States Patent
Suzuki et al.

(10) Patent No.: US 7,241,513 B2
(45) Date of Patent: Jul. 10, 2007

(54) FLUORENE COMPOUND AND ORGANIC LUMINESCENT DEVICE USING THE SAME

(75) Inventors: Koichi Suzuki, Kanagawa (JP); Mizuho Hiraoka, Kanagawa (JP); Akihiro Senoo, Kanagawa (JP); Naoki Yamada, Tokyo (JP); Chika Negishi, Kanagawa (JP); Akihito Saitoh, Kanagawa (JP); Daisaku Tanaka, Yamagata (JP); Ryoji Yashiro, Fukui (JP)

(73) Assignee: Canon Kabushiki Kaisha, Tokyo (JP)

( * ) Notice: Subject to any disclaimer, the term of this patent is extended or adjusted under 35 U.S.C. 154(b) by 204 days.

(21) Appl. No.: 10/491,745

(22) PCT Filed: Aug. 12, 2003

(86) PCT No.: PCT/JP03/10259

§ 371 (c)(1),
(2), (4) Date: Apr. 6, 2004

(87) PCT Pub. No.: WO2004/020372

PCT Pub. Date: Mar. 11, 2004

(65) Prior Publication Data

US 2004/0253389 A1 Dec. 16, 2004

(30) Foreign Application Priority Data

Aug. 27, 2002 (JP) .............................. 2002-246447

(51) Int. Cl.
H01L 51/54 (2006.01)
C09K 11/06 (2006.01)
C07C 13/567 (2006.01)

(52) U.S. Cl. ...................... 428/690; 428/917; 313/504; 313/506; 257/40; 257/E51.049; 257/E51.051; 585/27

(58) Field of Classification Search ..................... None
See application file for complete search history.

(56) References Cited

U.S. PATENT DOCUMENTS

| | | | |
|---|---|---|---|
| 4,539,507 A | 9/1985 | VanSlyke et al. | 313/504 |
| 4,720,432 A | 1/1988 | VanSlyke et al. | 428/457 |
| 4,885,211 A | 12/1989 | Tang et al. | 428/457 |
| 5,130,603 A | 7/1992 | Tokailin et al. | 313/504 |
| 5,151,629 A | 9/1992 | VanSlyke | 313/504 |
| 5,227,252 A | 7/1993 | Murayama et al. | 428/690 |
| 5,247,190 A | 9/1993 | Friend et al. | 257/40 |
| 5,317,169 A | 5/1994 | Nakano et al. | 257/40 |
| 5,382,477 A | 1/1995 | Saito et al. | 428/690 |
| 5,409,783 A | 4/1995 | Tang et al. | 428/690 |
| 5,514,878 A | 5/1996 | Holmes et al. | 257/40 |
| 5,672,678 A | 9/1997 | Holmes et al. | 528/373 |
| 5,726,457 A | 3/1998 | Nakano et al. | 257/40 |
| 6,093,864 A | 7/2000 | Tokailin et al. | 585/25 |
| 6,652,997 B2 | 11/2003 | Suzuki et al. | 428/690 |
| 6,929,870 B2 | 8/2005 | Ishida et al. | 428/690 |
| 2003/0039838 A1* | 2/2003 | Chen et al. | 428/411.1 |
| 2003/0087126 A1 | 5/2003 | Ishida et al. | 428/690 |
| 2003/0235713 A1 | 12/2003 | Suzuki et al. | 428/690 |
| 2005/0106414 A1* | 5/2005 | Saitoh et al. | 428/690 |

FOREIGN PATENT DOCUMENTS

| | | |
|---|---|---|
| EP | 1 221 434 | 7/2002 |
| JP | 58-128328 | 7/1983 |
| JP | 2-247278 | 10/1990 |
| JP | 3-255190 | 11/1991 |
| JP | 4-145192 | 5/1992 |
| JP | 5-202356 | 8/1993 |
| JP | 5-247460 | 9/1993 |
| JP | 9-202878 | 8/1997 |
| JP | 9-227576 | 9/1997 |
| JP | 11-111460 | 4/1999 |
| JP | 11-167991 A * | 6/1999 |
| JP | 2001-039933 | 2/2001 |
| JP | 2002-154993 | 5/2002 |
| JP | 2003-128651 | 5/2003 |

(Continued)

OTHER PUBLICATIONS

M.A. Baldo, et al., "Highly Efficient Phosphorescent Emission from Organic Electroluminescent Devices", Nature, vol. 395, pp. 151-153 (1998).

(Continued)

*Primary Examiner*—Marie Yamnitzky
(74) *Attorney, Agent, or Firm*—Fitzpatrick, Cella, Harper & Scinto

(57) ABSTRACT

A fluorene compound represented by the following general formula [I]:

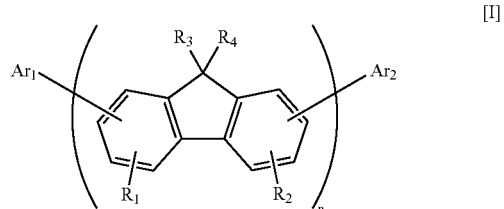

is used to provide an organic luminescent device. Such a device has an optical output exhibiting a high luminance with an extremely high efficiency, and has an extremely high durability.

11 Claims, 3 Drawing Sheets

FOREIGN PATENT DOCUMENTS

| | | |
|---|---|---|
| JP | 2003-229273 | 8/2003 |
| JP | 2004-042485 | 2/2004 |
| JP | 2004-043349 | 2/2004 |
| WO | 02/14244 | 2/2002 |

OTHER PUBLICATIONS

S. Ghosal, et al., "Formation of 1,3-Diynes and Biphenyls via the Copper (II) Nitrate Mediated Coupling of Organotin Compounds", J. Org. Chem., vol. 52, pp. 4296-4298 (1987).

C.W. Tang, et al., "Organic Electroluminescent Diodes", Appl. Phys. Lett., vol. 51, pp. 913-915.

T. Yamamoto, et al., "A Novel Type of Polycondensation Utilizing Transition Metal-Catalyzed C-C Coupling", Bull. Chem. Soc. Jap., vol. 51, pp. 2091-2097 (1978).

J.H. Burroughes, et al., "Light-Emitting Diodes Based on Conjugated Polymers", Nature, vol. 347, pp. 539-541 (1990).

N. Miyaura, et al., "Palladium-Catalyzed Cross-Coupling Reactions of Organaboron Compounds", Chem. Reviews, vol. 95, pp. 2457-2483 (1978).

Tokito, S., et al.; "Acene Containing Polyfluorenes for Red, Green and Blue Emission in Organic Light-Emitting Diodes"; PROC. SPIE, vol. 4105, pp. 69-74 (2001).

* cited by examiner

FLUORENE COMPOUND AND ORGANIC LUMINESCENT DEVICE USING THE SAME

This is a national stage of PCT/JP03/10259 filed Aug. 12, 2003.

TECHNICAL FIELD

The present invention relates to a novel organic compound and an organic luminescent device using the same.

BACKGROUND ART

An organic luminescent device is a device where a thin film containing a fluorescent organic compound or a phosphorescent organic compound is sandwiched between an anode and a cathode; an electron and a hole injected from the respective electrodes generate an exciton of the fluorescent compound or the phosphorescent compound; and light emitted when the exciton returns to a ground state is utilized.

According to a study of Kodak company in 1987 (Appl. Phys. Lett. 51, 913 (1987)), there has been reported a luminescence of approximately 1000 cd/m² at an applied voltage of approximately 10 V in a device having a separated-function type two-layer structure using ITO as an anode, a magnesium-silver alloy as a cathode, an aluminum quinolinol complex as an electron transport material and a luminescent material, and a triphenyl amine derivative as a hole transport material. The related patents include U.S. Pat. Nos. 4,539,507, 4,720,432, 4,885,211, and so on.

In addition, it is possible to generate a luminescence from ultraviolet to infrared ones by changing the kinds of the fluorescent organic compound, and in recent years, extensive studies have been made on various kinds of compounds. For instance, such compounds are disclosed in U.S. Pat. Nos. 5,151,629, 5,409,783 and 5,382,477, Japanese Patent Application Laid-Open Nos. 2-247278, 3-255190, 5-202356, 9-202878, 9-227576, and so on.

In recent years, many studies have been made on an application of energy in a triplet state to an EL using phosphorescent compounds as luminescent materials. A high luminous efficiency exhibited by an organic luminescent device using an iridium complex as a luminescent material has been reported by a group at Princeton University (Nature 395, 151 (1998)).

Furthermore, in addition to the organic luminescent device using a low molecular weight material as mentioned above, an organic luminescent device using a conjugated polymer has been reported by a group at Cambridge University (Nature, 347, 539 (1990)). In this report, a luminescence from a single layer is confirmed through film formation of polyphenylene vinylene (PPV) using a coating system.

The related patents of the organic luminescent device using the conjugated polymer include U.S. Pat. Nos. 5,247,190, 5,514,878, 5,672,678, Japanese Patent Application Laid-Open Nos. 4-145192 and 5-247460, and so on.

In this way, a recent progress in the organic luminescent device is remarkable, and characteristics thereof suggest a possibility of applications for various purposes, which enable the luminescent device with a high luminance even at a low applied voltage, a wide variety of luminous wavelengths, a high-speed response, and a thin and lightweight form.

However, an optical output with a higher luminance or higher conversion efficiency is required under the present conditions. In addition, many problems still remain to be solved regarding a durability against a change with time due to a long-term use, deterioration caused by an atmospheric gas containing oxygen, moisture, or the like. Furthermore, it is not still insufficient for solving problems related to the needs for luminescences of blue, green, and red having high color purity when considering the applications to a full color display and the like.

DISCLOSURE OF THE INVENTION

An object of the present invention is to provide a novel fluorene compound.

Also, another object of the present invention is to provide an organic luminescent device using a specific fluorene compound, which has an optical output with an extremely high efficiency and a high luminance.

In addition, another object of the present invention is to provide an organic luminescent device having an extremely high durability.

Furthermore, another object of the present invention is to provide an organic luminescent device that can be easily produced at relatively low costs.

Accordingly, a fluorene compound according to the present invention is represented by the following general formula [I]:

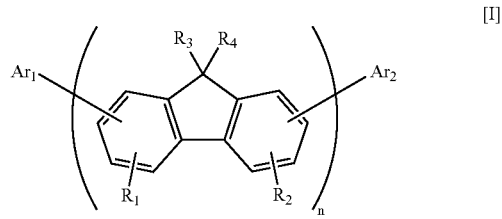

(wherein $R_1$ and $R_2$ represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom, in which $R_1$ themselves or $R_2$ themselves which are bonded to different fluorene groups may be identical to or different from each other and $R_1$ and $R_2$ which are bonded to the same fluorene group may be identical to or different from each other; $R_3$ and $R_4$ represent a hydrogen atom, a substituted or unsubstituted alkyl group, a substituted or unsubstituted aralkyl group, a substituted or unsubstituted aryl group, or a substituted or unsubstituted heterocyclic group, in which $R_3$ themselves or $R_4$ themselves which are bonded to different fluorene groups may be identical to or different from each other and $R_3$ and $R_4$ which are bonded to the same fluorene group may be identical to or different from each other; $Ar_1$ and $Ar_2$ represent a substituted or unsubstituted fused polycyclic aromatic group having at least three benzene rings in total or a substituted or unsubstituted fused polycyclic heterocyclic group bonded to the fluorene group with a carbon atom and having at least three rings including a benzene ring and a heterocyclic ring in total, in which Ar$_1$ and Ar$_2$ may be identical to or different from each other; and n represents an integer of 1 to 10, preferably 1 to 3.)

Further, as a preferable form, an organic luminescent device according to the present invention includes at least a pair of electrodes including an anode and a cathode and one or a plurality of layers containing an organic compound sandwiched between the pair of electrodes, in which at least one of the layers containing the organic compound contains at least one of the fluorene compounds.

BEST MODE FOR CARRYING OUT THE INVENTION

Figure 1:
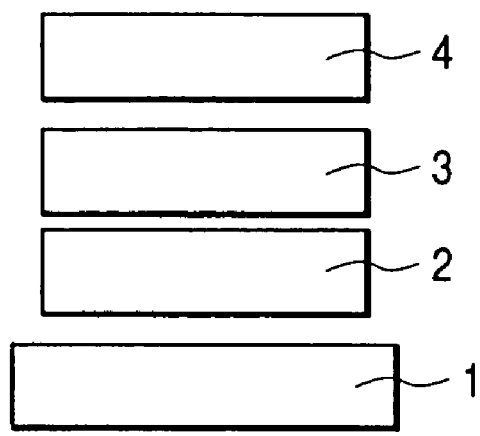
FIG. 1 is a cross-sectional view showing an example of the organic luminescent device in accordance with the present invention.

Hereinafter, the present invention will be described in detail.

First, the fluorene compound of the present invention will be described.

The fluorene compound of the present invention is represented by the above general formula [I].

Here, at least one of Ar$_1$ and Ar$_2$ is preferably a fused polycyclic aromatic group represented by the following general formula [II]:

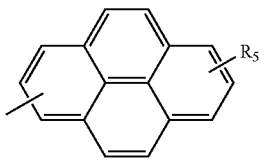

[II]

(wherein R$_5$ represents a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom.)

Furthermore, the fluorene compound of the present invention is more preferably represented by one of the following structural formulas:

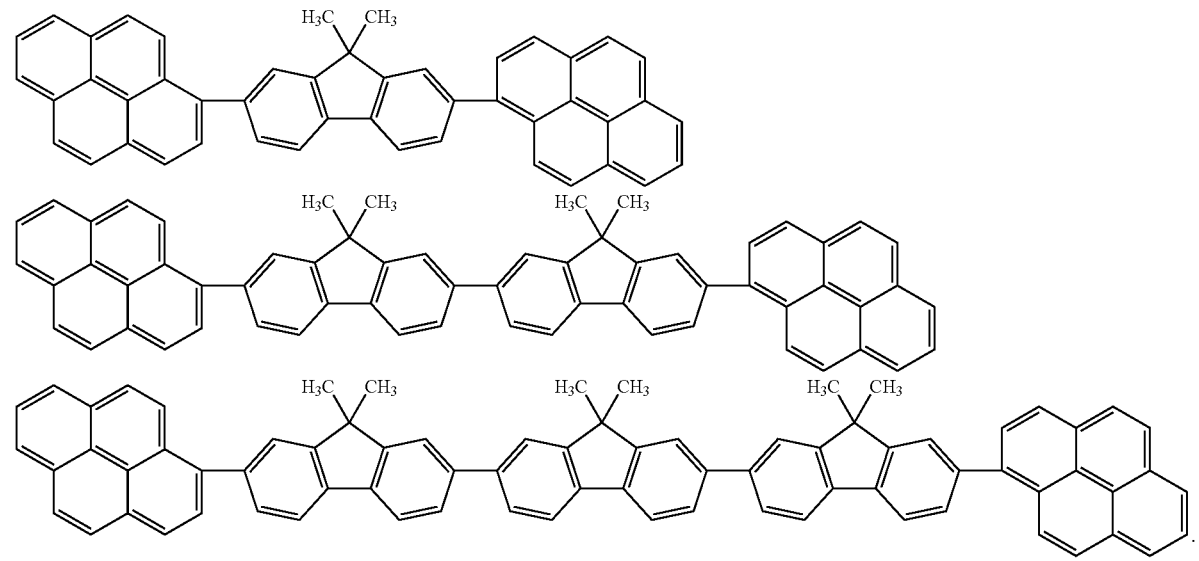

Further, at least one of Ar$_1$ and Ar$_2$ is preferably a fused polycyclic aromatic group represented by one of the following general formulae [III] to [IX]:

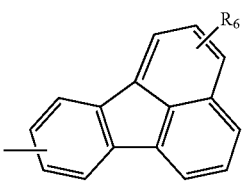

[III]

-continued

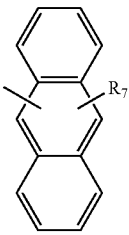
[IV]

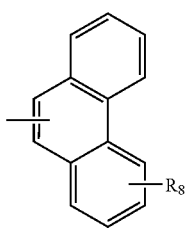
[V]

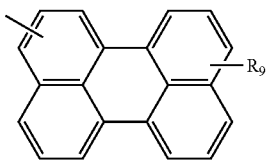
[VI]

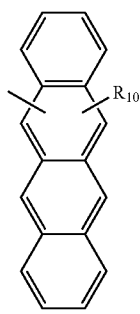
[VII]

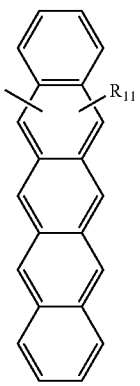
[VIII]

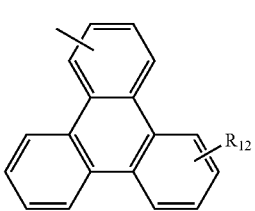
[IX]

(wherein $R_6$ to $R_{12}$ represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom.)

Specific examples of substituents in the above general formula [I] to the above general formula [IX] will be shown below.

As the alkyl group, a methyl group, an ethyl group, an n-propyl group, an isopropyl group, an n-butyl group, a tert-butyl group, an octyl group, and the like can be given.

As the aralkyl group, a benzyl group, a phenethyl group, and the like can be given.

As the aryl group, a phenyl group, a biphenyl group, a terphenyl group, and the like can be given.

As the heterocyclic group, a thienyl group, a pyrrolyl group, a pyridyl group, an oxazolyl group, an oxadiazolyl group, a thiazolyl group, a thiadiazolyl group, a terthienyl group, and the like can be given.

As the substituted amino group, a dimethylamino group, a diethylamino group, a dibenzylamino group, a diphenylamino group, a ditolylamino group, a dianisolylamino group, and the like can be given.

As the halogen atom, fluorine, chlorine, bromine, iodine, and the like can be given.

As the fused polycyclic aromatic group, a fluorenyl group, a naphthyl group, a fluoranthenyl group, an anthryl group, a phenanthryl group, a pyrenyl group, a tetracenyl group, a pentacenyl group, a triphenylenyl group, a perylenyl group, and the like can be given.

As the fused polycyclic heterocyclic group, a carbazolyl group, an acridinyl group, a phenanthrolyl group, and the like can be given.

As substituents which the above-mentioned substituents may have, alkyl groups such as a methyl group, an ethyl group, and a propyl group; aralkyl groups such as a benzyl group and a phenethyl group; aryl groups such as a phenyl group and a biphenyl group; heterocyclic groups such as a thienyl group, a pyrrolyl group, and a pyridyl group; amino groups such as a dimethylamino group, a diethylamino group, a dibenzylamino group, a diphenylamino group, a ditolylamino group, and a dianisolylamino group; alkoxyl groups such as a methoxyl group, an ethoxyl group, a propoxyl group, and a phenoxyl group; a cyano group; halogen atoms such as fluorine, chlorine, bromine, and iodine; and the like can be given.

Next, typical examples of the fluorene compound of the present invention will be hereinafter given.

However, the present invention is not limited thereto.

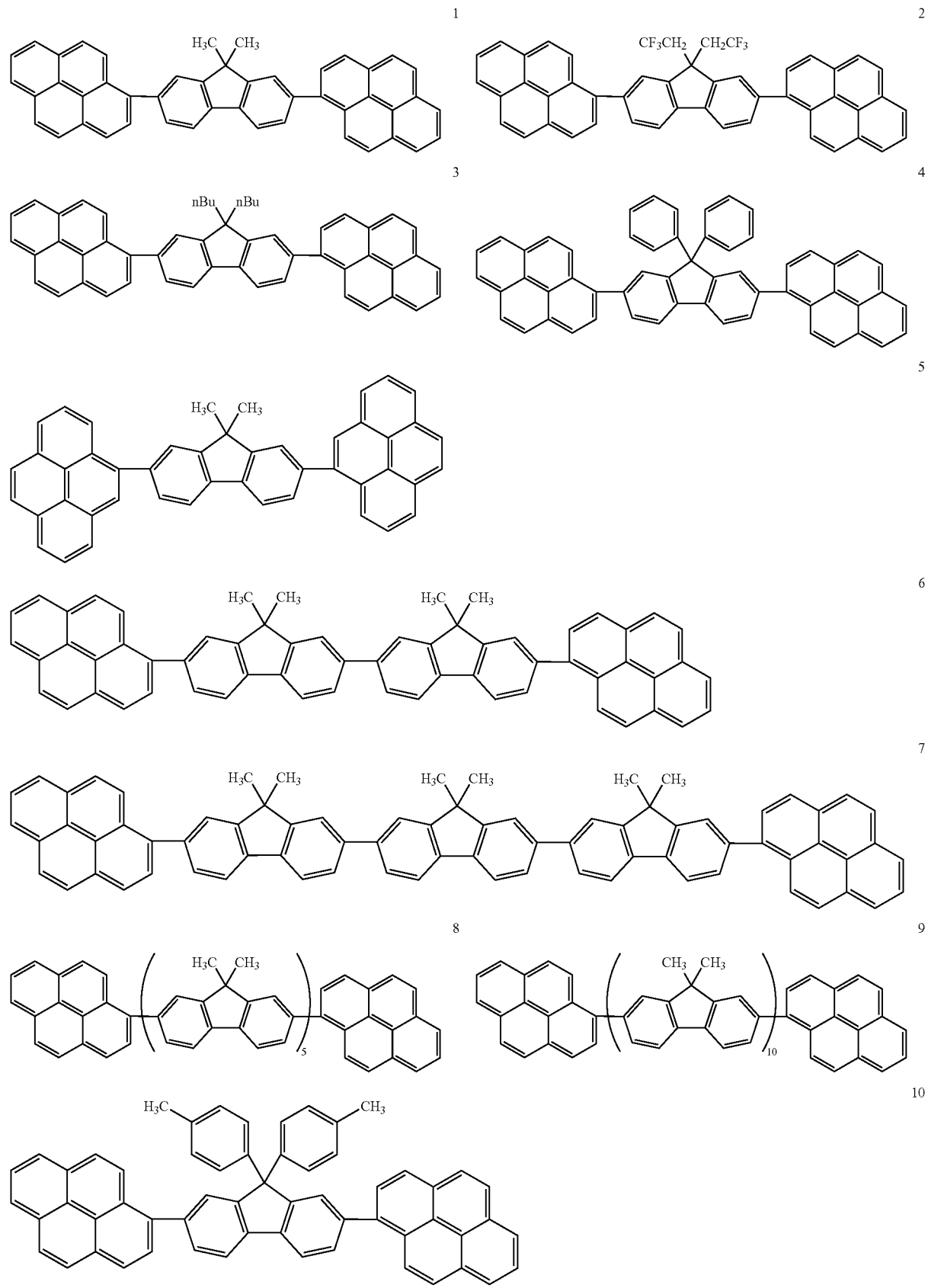

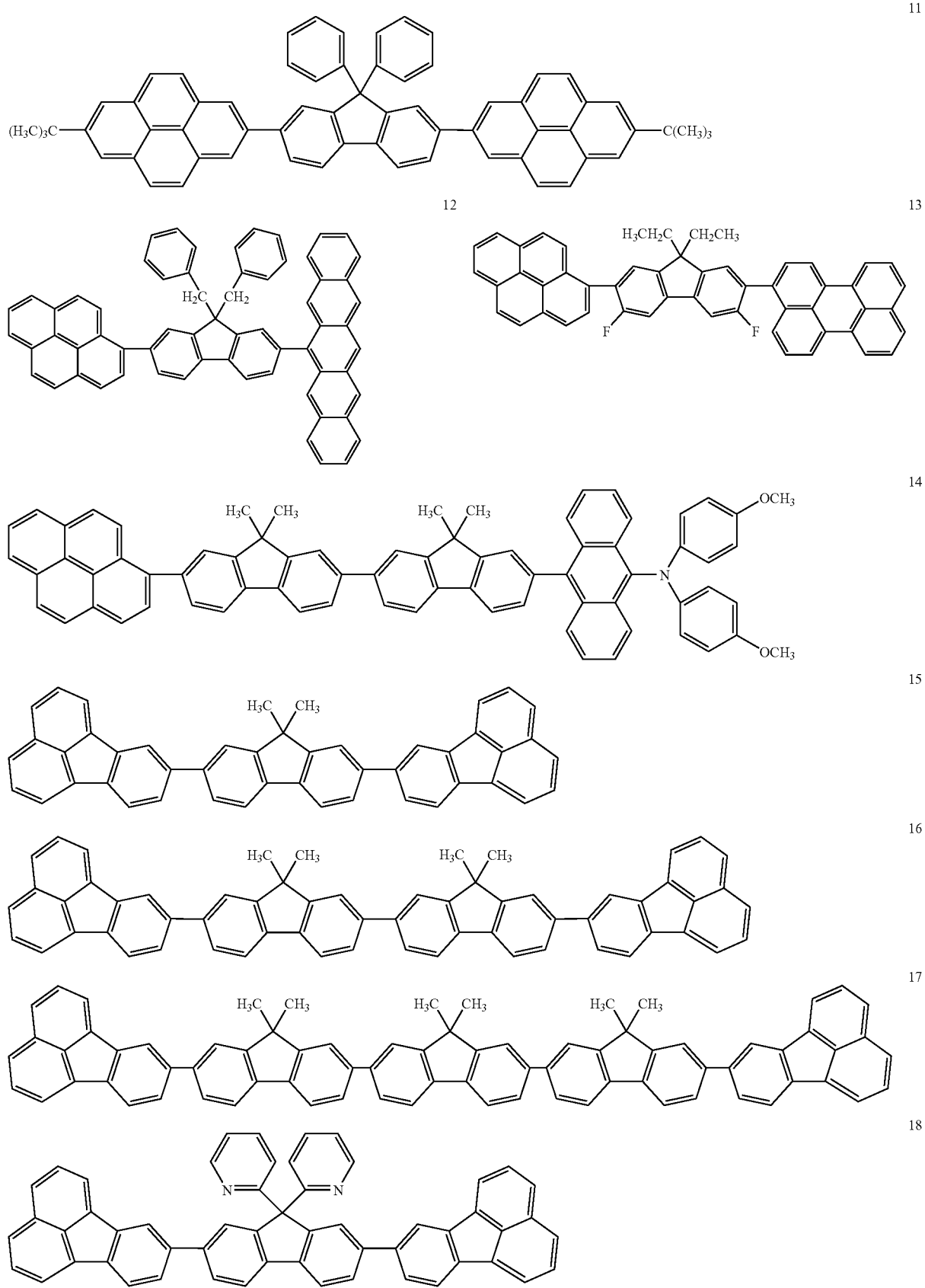

-continued
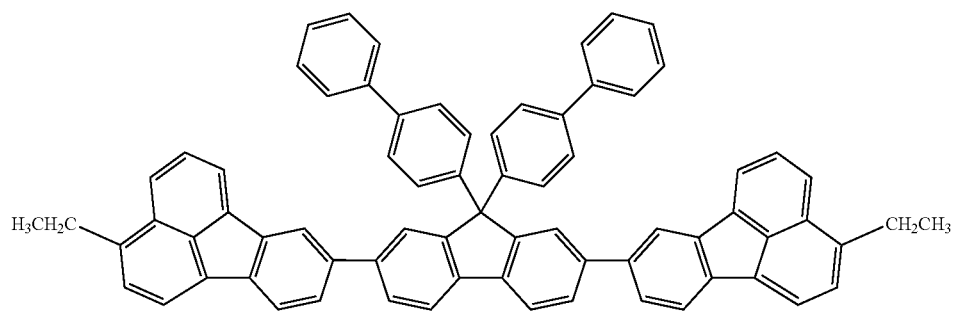
19
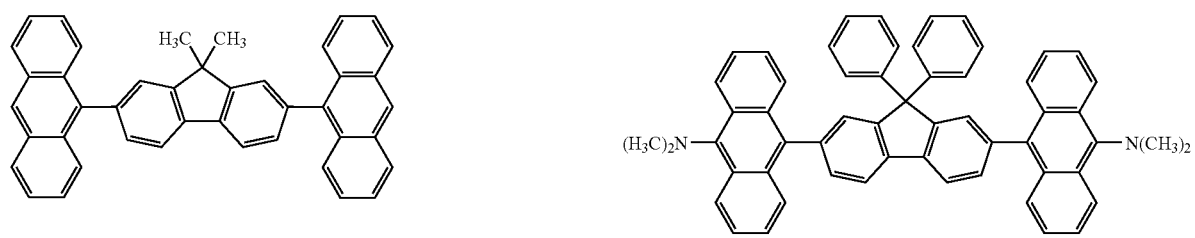
20
21
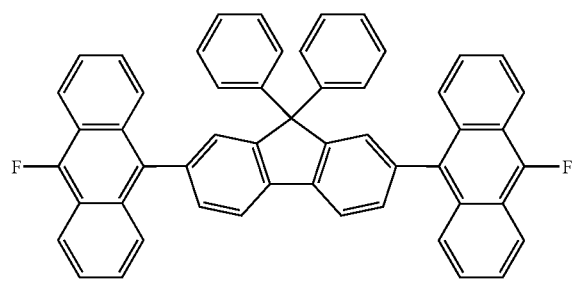
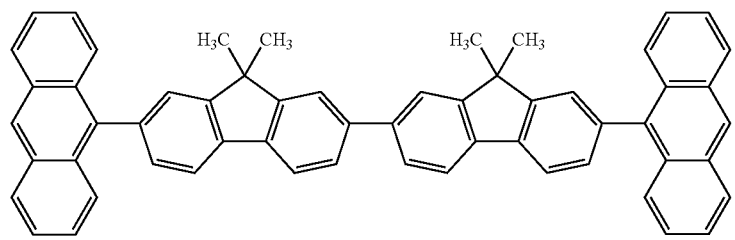
22
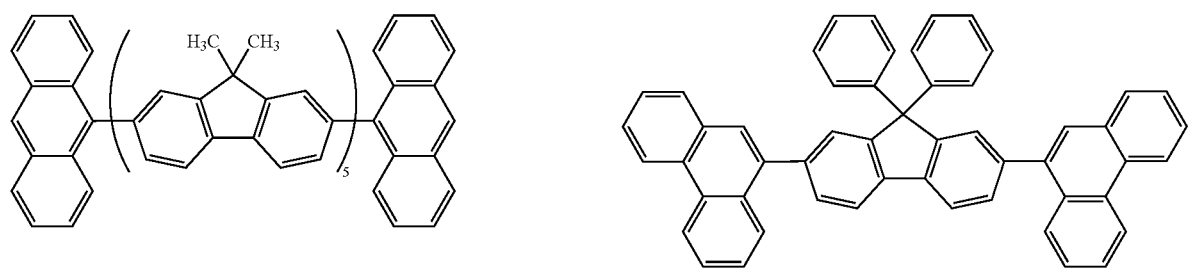
23
24
25
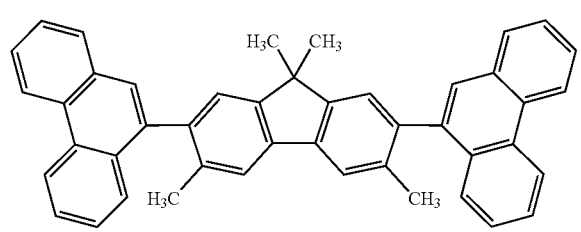
26

-continued
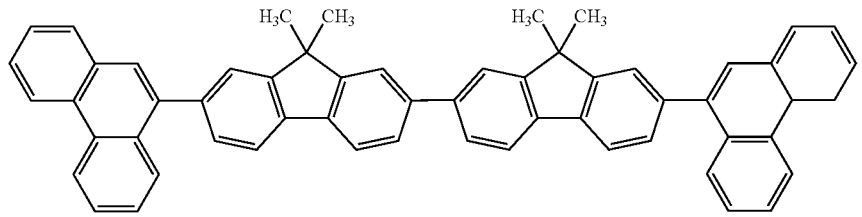
27
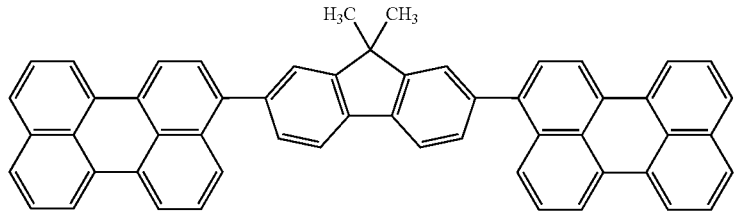
28
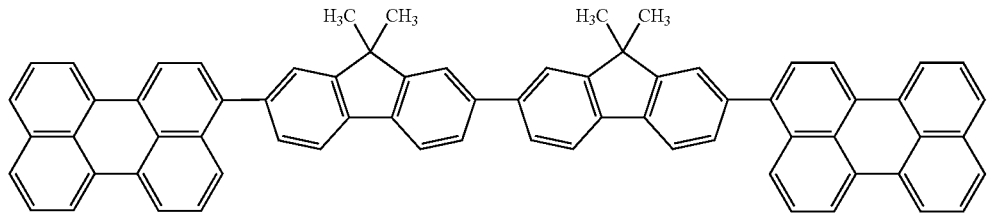
29
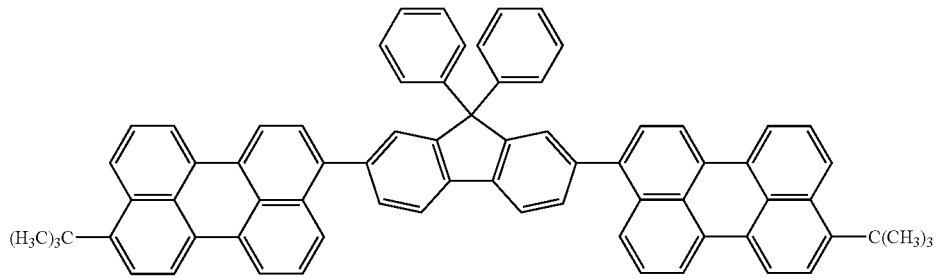
30
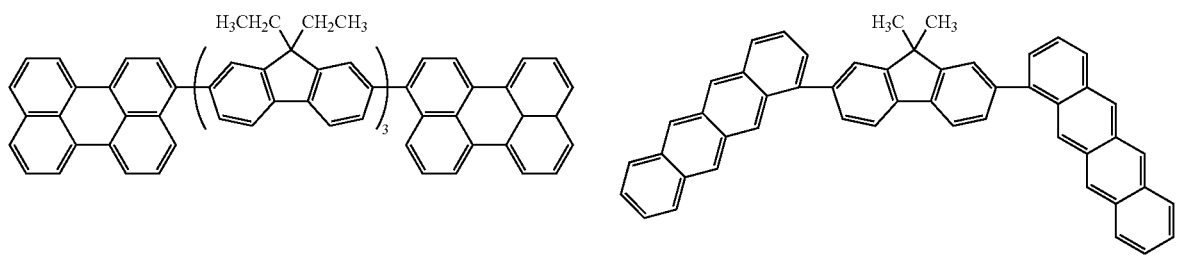
31
32
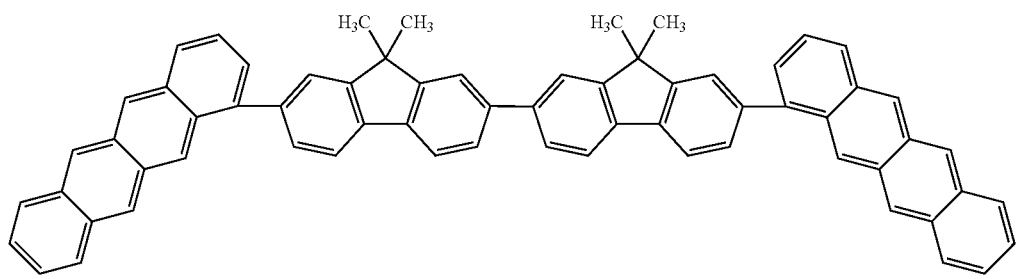
33

-continued

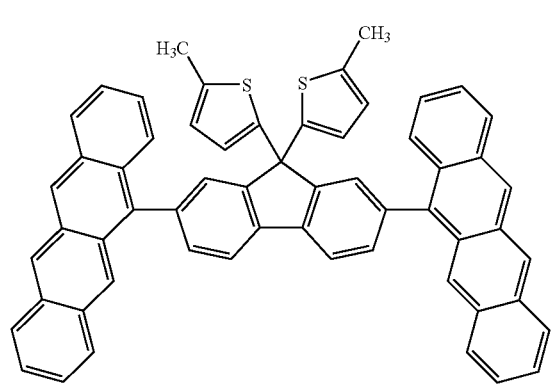
34

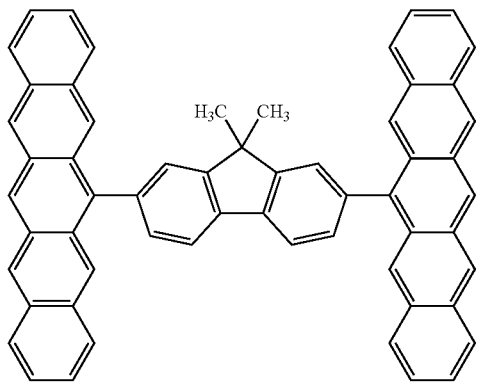
35

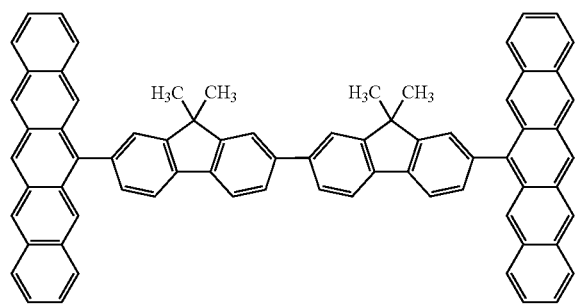
36

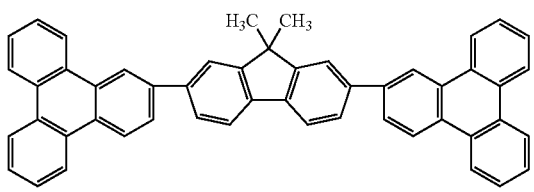
37

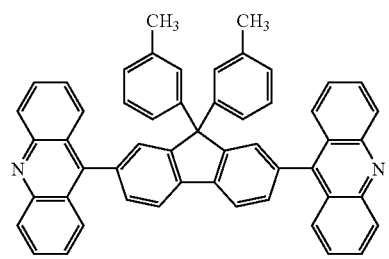
38

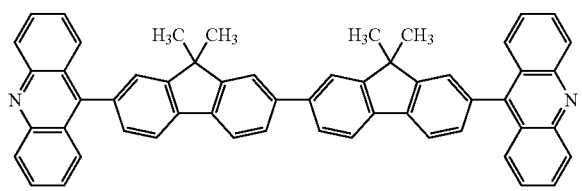
39

The fluorene compound of the present invention can be synthesized by a well-known method and obtained by using, for example, a synthesis method such as Suzuki coupling method (e.g., Chem. Rev. 1995, 95, 2457-2483) using a palladium catalyst, Yamamoto method (e.g., Bull. Chem. Soc. Jpn. 51, 2091, 1978) using a nickel catalyst, or a method in which a synthesis is performed by using a tin aryl compound (e.g., J. Org. Chem., 52, 4296, 1987).

The fluorene compound of the present invention is superior to the conventional compounds in electron transport property, luminescence property, and durability, which is useful for a layer containing an organic compound of an organic luminescent device, in particular, an electron transport layer and a luminescent layer, and a layer formed by a vacuum evaporation method, a solution-coating method, etc., is hard to undergo crystallization or the like and is excellent in stability with time.

Next, the organic luminescent device of the present invention will be described in detail.

The organic luminescent device of the present invention includes at least a pair of electrodes including an anode and a cathode and one or a plurality of layers containing an organic compound sandwiched between the pair of electrodes, in which at least one of the layers containing the organic compound contains at least one of the fluorene compounds represented by the above general formula [I].

In the organic luminescent device of the present invention, it is preferable that at least an electron transport layer or a luminescent layer among the organic compound-containing layers contain at least one of the fluorene compounds.

In the organic luminescent device of the present invention, the fluorene compound represented by the above general formula [I] is formed between the anode and the cathode by the vacuum evaporation method or the solution-coating method. The organic layer is preferably formed into a thin film with a thickness of less than 10 μm, more preferably 0.5 μm or less, much more preferably 0.01 to 0.5 μm.

Further, according to a preferable mode of the organic luminescent device of the present invention, at least a luminescent layer among the layers containing the organic compound includes at least one of the fluorene compounds represented by the above general formula [I] and one of arylamine compounds represented by the following general formulae [X] to [XIV] and an acetylene compound represented by the following general formula [XV]:

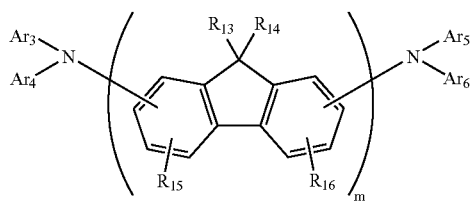

(wherein $R_{13}$ and $R_{14}$ represent a hydrogen atom, a substituted or unsubstituted alkyl group, a substituted or unsubstituted aralkyl group, a substituted or unsubstituted aryl group, or a substituted or unsubstituted heterocyclic group, in which $R_{13}$ themselves or $R_{14}$ themselves which are bonded to different fluorene groups may be identical to or different from each other and $R_{13}$ and $R_{14}$ which are bonded to the same fluorene group may be identical to or different from each other; $R_{15}$ and $R_{16}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, in which $R_{15}$ themselves or $R_{16}$ themselves which are bonded to different fluorene groups may be identical to or different from each other and $R_{15}$ and $R_{16}$ which are bonded to the same fluorene group may be identical to or different from each other; $Ar_3$, $Ar_4$, $Ar_5$, and $Ar_6$ represent a substituted or unsubstituted aromatic group, a substituted or unsubstituted heterocyclic group, a substituted or unsubstituted fused polycyclic aromatic group, or a substituted or unsubstituted fused polycyclic heterocyclic group, in which $Ar_3$, $Ar_4$, $Ar_5$, and $Ar_6$ may be identical to or different from one another and $Ar_3$, $Ar_4$, $Ar_5$, and $Ar_6$ may be bonded with one another to form a ring; and m represents an integer of 1 to 10);

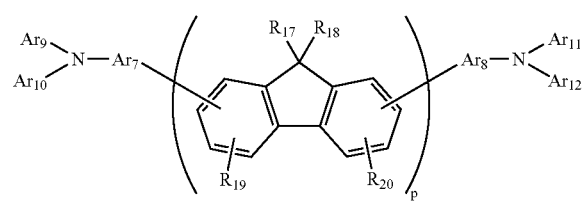

(wherein $R_{17}$ and $R_{18}$ represent a hydrogen atom, a substituted or unsubstituted alkyl group, a substituted or unsubstituted aralkyl group, a substituted or unsubstituted aryl group, or a substituted or unsubstituted heterocyclic group, in which $R_{17}$ themselves or $R_{18}$ themselves which are bonded to different fluorene groups may be identical to or different from each other and $R_{17}$ and $R_{18}$ which are bonded to the same fluorene group may be identical to or different from each other; $R_{19}$ and $R_{20}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, in which $R_{19}$ themselves or $R_{20}$ themselves which are bonded to different fluorene groups may be identical to or different from each other and $R_{19}$ and $R_{20}$ which are bonded to the same fluorene group may be identical to or different from each other; $Ar_7$ and $Ar_8$ represent a divalent substituted or unsubstituted aromatic group or a substituted or unsubstituted heterocyclic group, in which $Ar_7$ and $Ar_8$ may be identical to or different from each other; $Ar_9$, $Ar_{10}$, $Ar_{11}$, and $Ar_{12}$ represent a substituted or unsubstituted aromatic group, a substituted or unsubstituted heterocyclic group, a substituted or unsubstituted fused polycyclic aromatic group, or a substituted or unsubstituted fused polycyclic heterocyclic group, in which $Ar_9$, $Ar_{10}$, $Ar_{11}$, and $Ar_{12}$ may be identical to or different from one another and $Ar_9$, $Ar_{10}$, $Ar_{11}$, and $Ar_{12}$ may be bonded with one another to form a ring; and p represents an integer of 1 to 10);

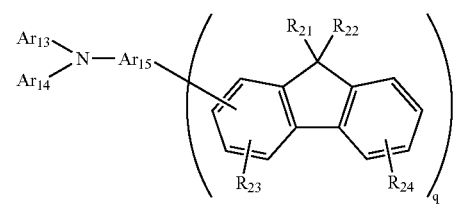

(wherein $R_{21}$ and $R_{22}$ represent a hydrogen atom, a substituted or unsubstituted alkyl group, a substituted or unsubstituted aralkyl group, a substituted or unsubstituted aryl group, or a substituted or unsubstituted heterocyclic group, in which $R_{21}$ themselves or $R_{22}$ themselves which are bonded to different fluorene groups may be identical to or different from each other and $R_{21}$ and $R_{22}$ which are bonded to the same fluorene group may be identical to or different from each other; $R_{23}$ and $R_{24}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, in which $R_{23}$ themselves or $R_{24}$ themselves which are bonded to different fluorene groups may be identical to or different from each other and $R_{23}$ and $R_{24}$ which are bonded to the same fluorene group may be identical to or different from each other; $Ar_{13}$ and $Ar_{14}$ represent a substituted or unsubstituted aromatic group, a substituted or unsubstituted heterocyclic group, a substituted or unsubstituted fused polycyclic aromatic group, or a substituted or unsubstituted fused polycyclic heterocyclic group, in which $Ar_{13}$ and $Ar_{14}$ may be identical to or different from each other and $Ar_{13}$ and $Ar_{14}$ may be bonded to each other to form a ring; $Ar_{15}$ represents a divalent substituted or unsubstituted aromatic group or a substituted or unsubstituted heterocyclic group; and q represents an integer of 1 to 10);

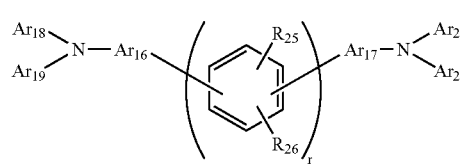

(wherein $R_{25}$ and $R_{26}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, in which $R_{25}$ themselves or $R_{26}$ themselves which are bonded to different phenylene groups may be identical to or different from each other and $R_{25}$ and $R_{26}$ which are bonded to the same phenylene group may be identical to or different from each other; $Ar_{16}$ and $Ar_{17}$ represent a divalent substituted or unsubstituted aromatic group or a substituted or unsubstituted heterocyclic group, in which $Ar_{16}$ and $Ar_{17}$ may be identical to or different from each other; $Ar_{18}$, $Ar_{19}$, $Ar_{20}$, and $Ar_{21}$ represent a substituted or unsubstituted aromatic group, a substituted or unsubstituted heterocyclic group, a substituted or unsubstituted fused polycyclic aromatic group, or a substituted or unsubstituted fused polycyclic heterocyclic group, in which $Ar_{18}$, $Ar_{19}$, $Ar_{20}$, and $Ar_{21}$ may be identical to or different from one another and $Ar_{18}$, $Ar_{19}$, $Ar_{20}$, and $Ar_{21}$ may be bonded with one another to form a ring; and r represents an integer of 1 to 10);

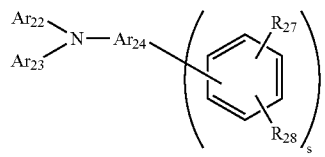

[XIV]

(wherein $R_{27}$ and $R_{28}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, in which $R_{27}$ themselves or $R_{28}$ themselves which are bonded to different phenylene groups may be identical to or different from each other and $R_{27}$ and $R_{28}$ which are bonded to the same phenylene group may be identical to or different from each other; $Ar_{22}$ and $Ar_{23}$ represent a substituted or unsubstituted aromatic group, a substituted or unsubstituted heterocyclic group, a substituted or unsubstituted fused polycyclic aromatic group, or a substituted or unsubstituted fused polycyclic heterocyclic group, in which $Ar_{22}$ and $Ar_{23}$ may be identical to or different from each other and $Ar_{22}$ and $Ar_{23}$ may be bonded to each other to form a ring; $Ar_{24}$ represents a divalent substituted or unsubstituted aromatic group or a substituted or unsubstituted heterocyclic group; and s represents an integer of 1 to 10); and

[XV]

(wherein $Ar_{25}$ and $Ar_{26}$ represent a substituted or unsubstituted aromatic group, a substituted or unsubstituted heterocyclic group, a substituted or unsubstituted fused polycyclic aromatic group, or a substituted or unsubstituted fused polycyclic heterocyclic group, in which $Ar_{25}$ and $Ar_{26}$ may be identical to or different from each other; and t represents an integer of 1 to 5.)

Specific examples of substituents in the general formulae [X] to [XV] are the same as those exemplified in the above general formulae [I] to [IX]. Typical examples of the arylamine compounds represented by the general formulae [X] to [XIV] and the acetylene compound represented by the general formula [XV] will be given below, but the present invention is not limited thereto.

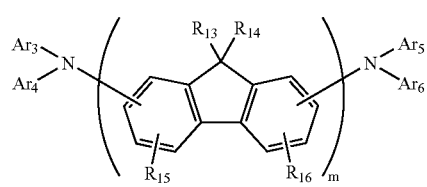

[X]

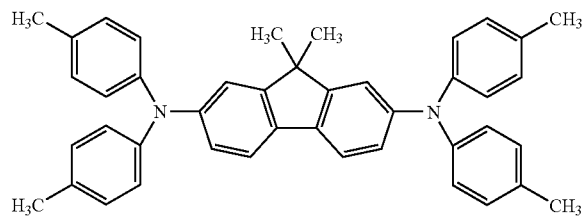

AA-1

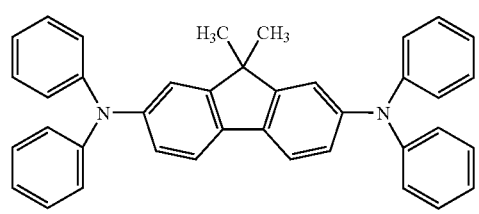

AA-2

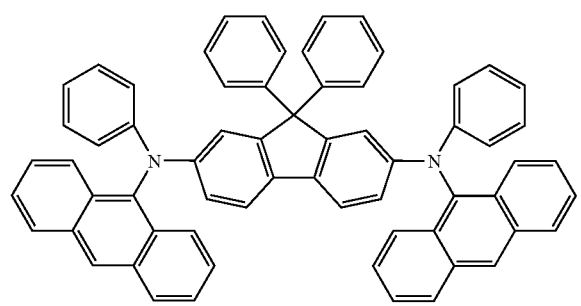

AA-3

-continued
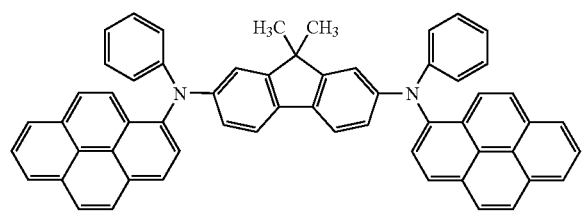 AA-4
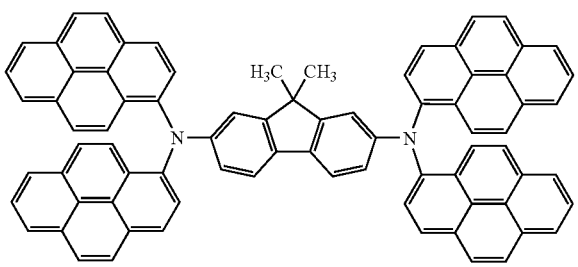 AA-5
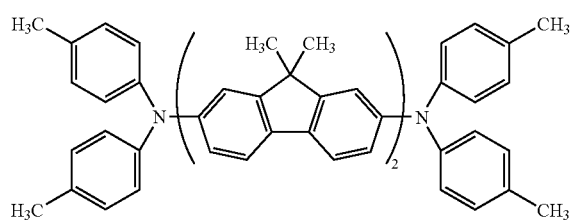 AA-6
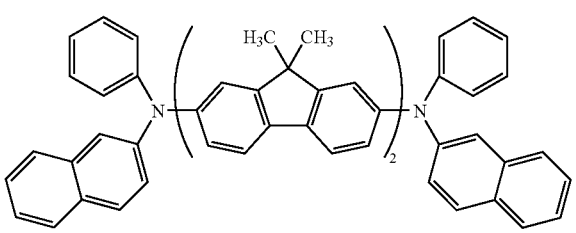 AA-7
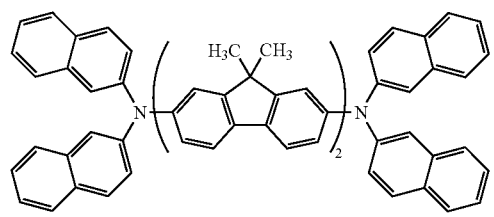 AA-8
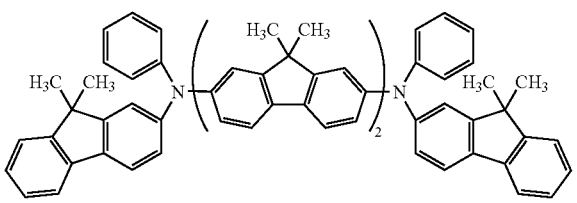 AA-9
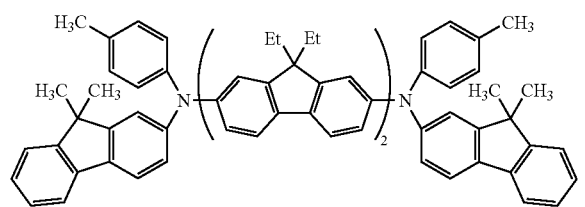 AA-10
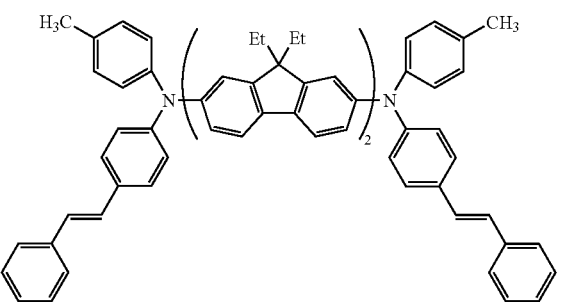 AA-11
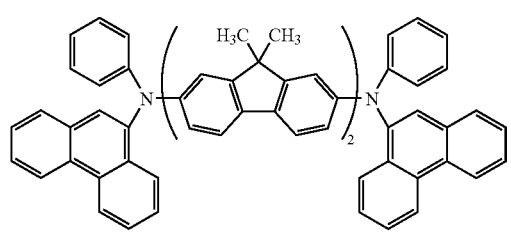 AA-12
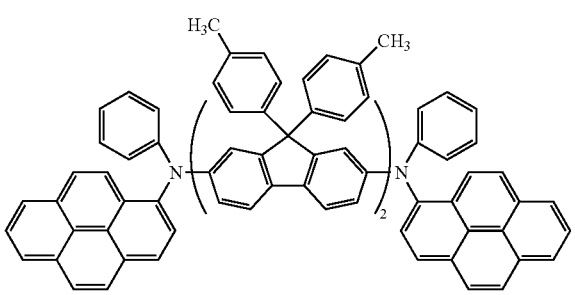 AA-13

-continued
AA-14
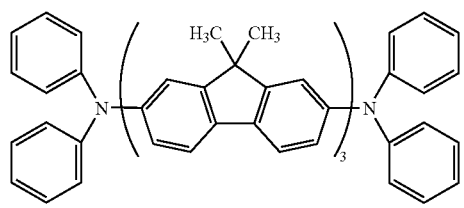
AA-15
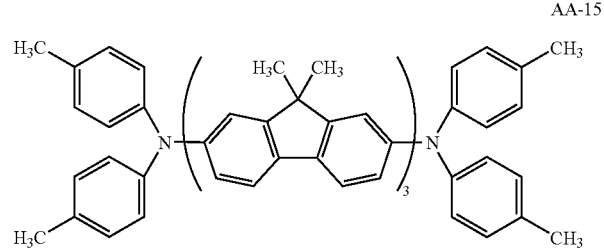
AA-16
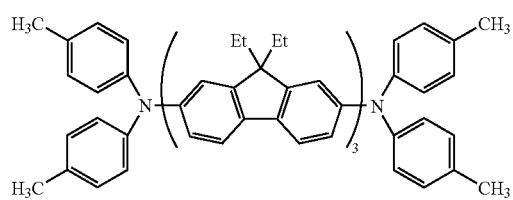
AA-17
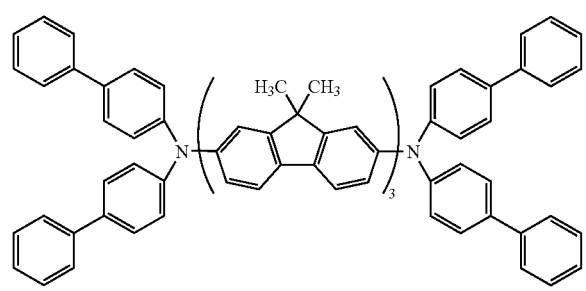
AA-18
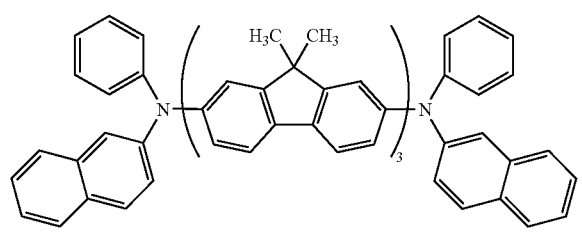
AA-19
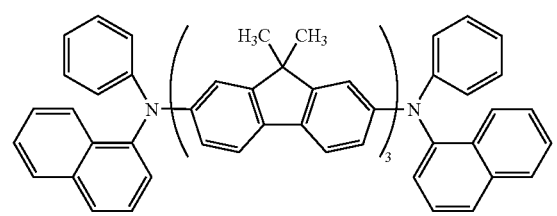
AA-20
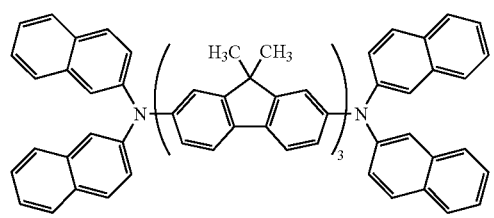
AA-21
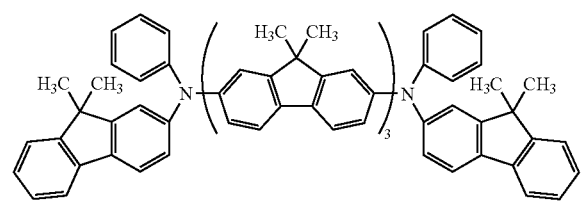
AA-22
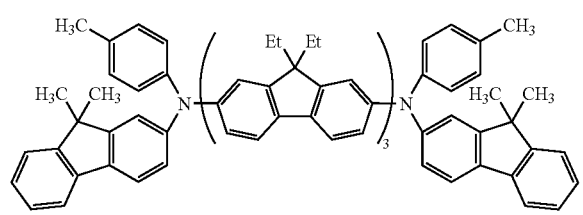
AA-23
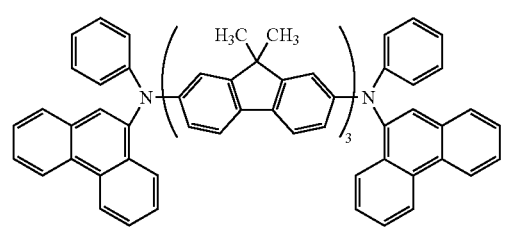

-continued
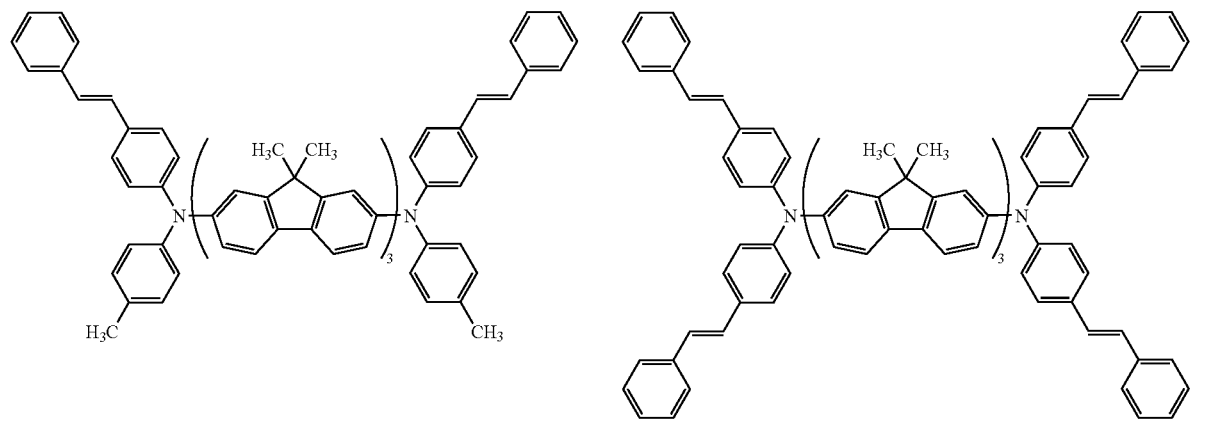
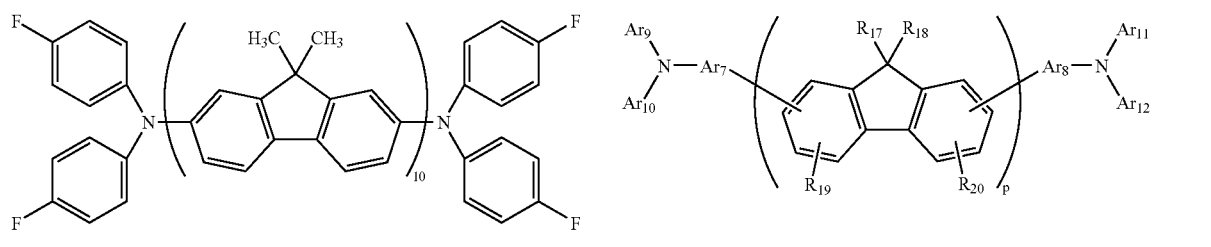
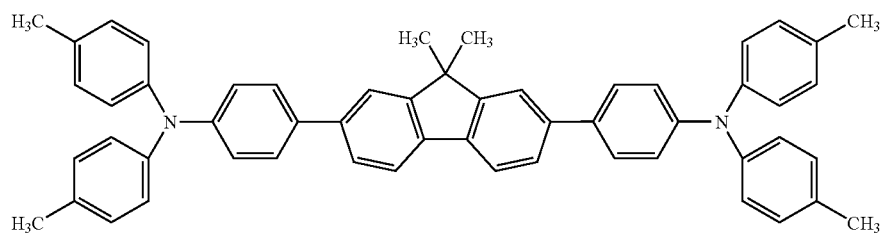
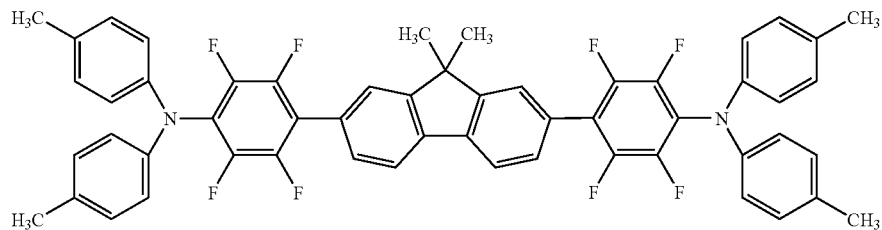
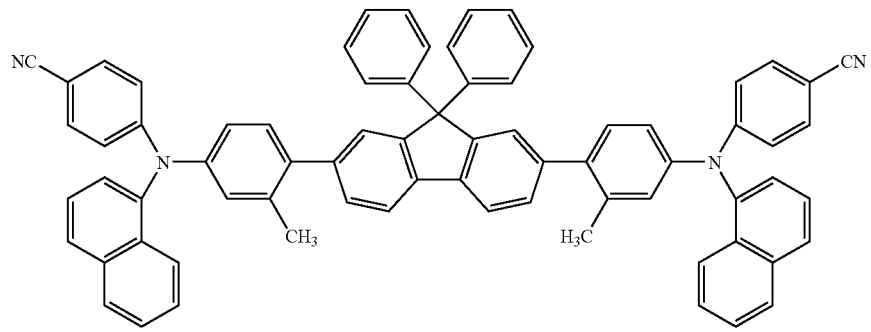

-continued
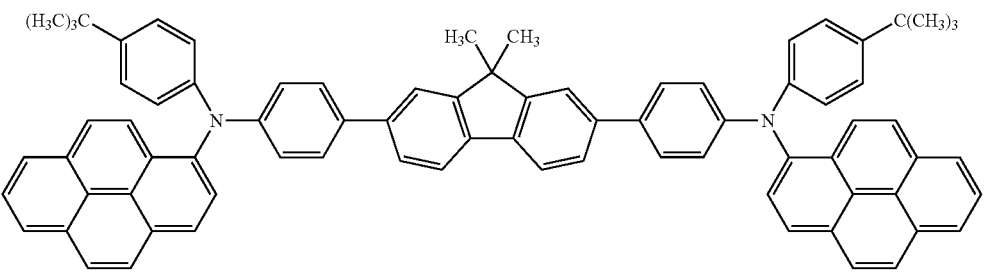
AA-31
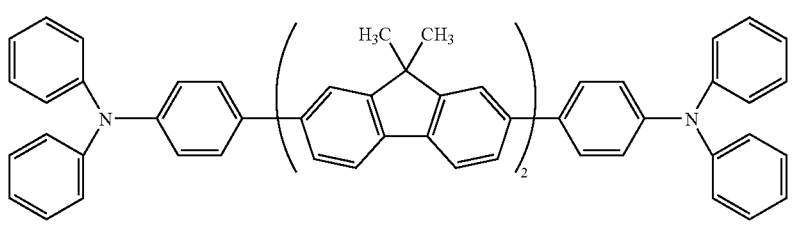
AA-32
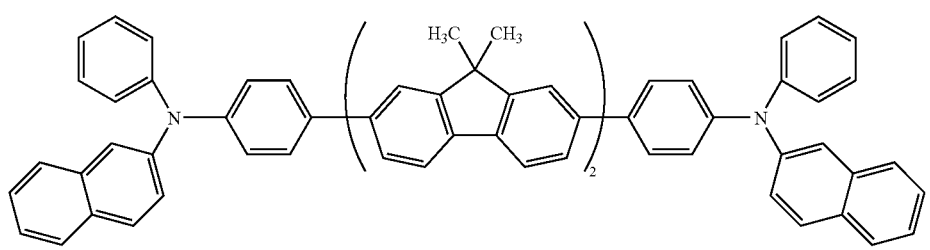
AA-33
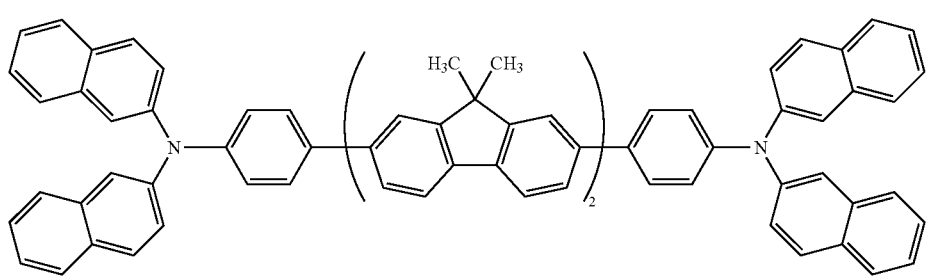
AA-34
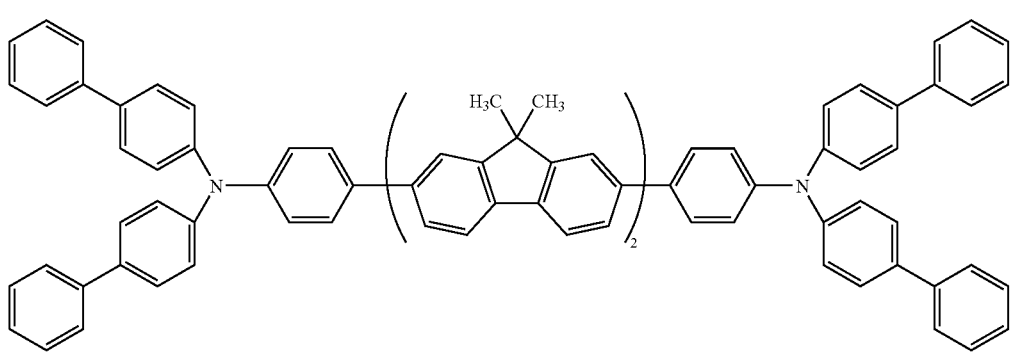
AA-35
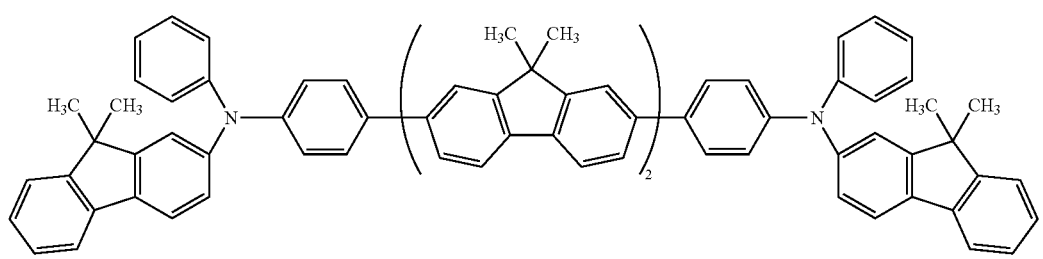
AA-36

-continued
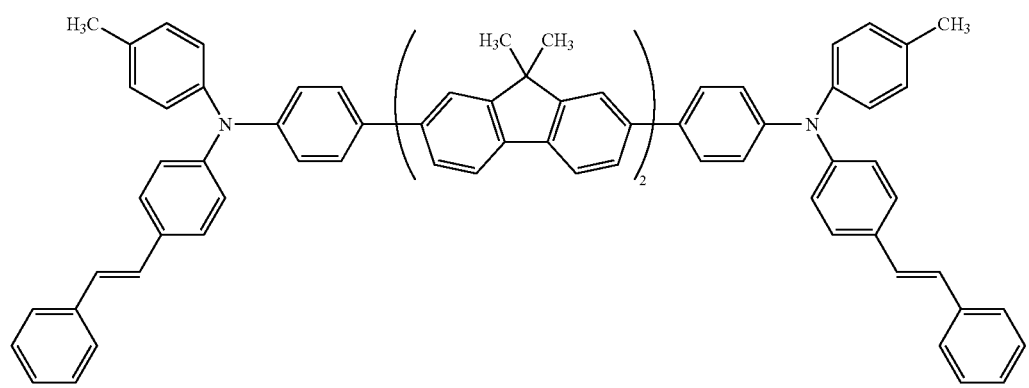
AA-37
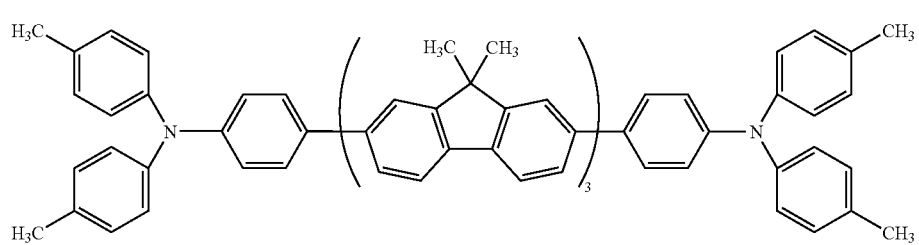
AA-38
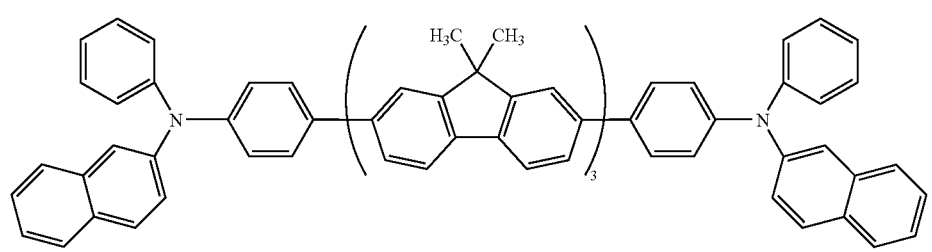
AA-39
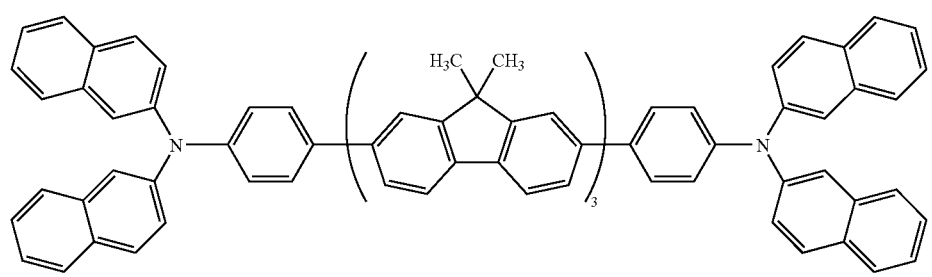
AA-40
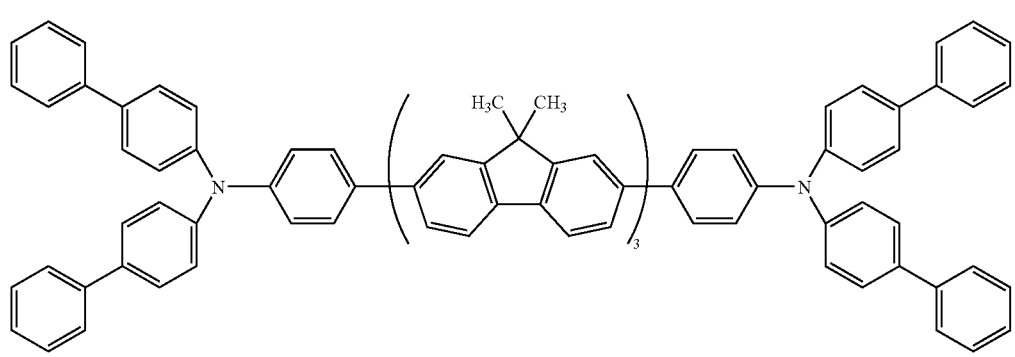
AA-41

-continued
AA-42
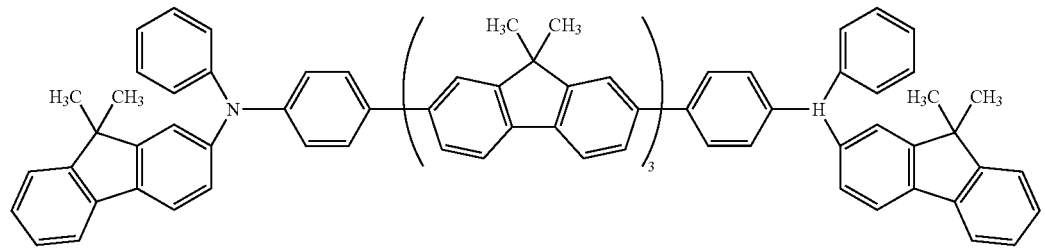
AA-43
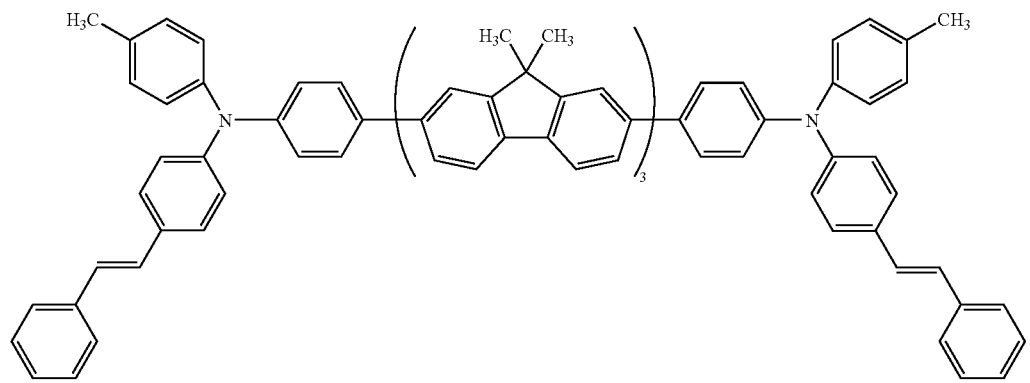
A-44
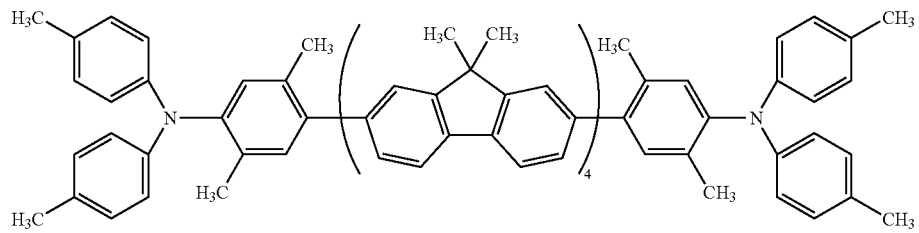
AA-45
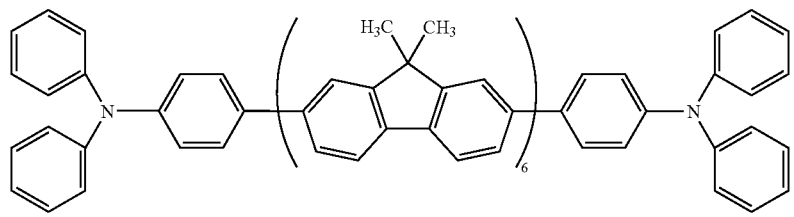
AA-46
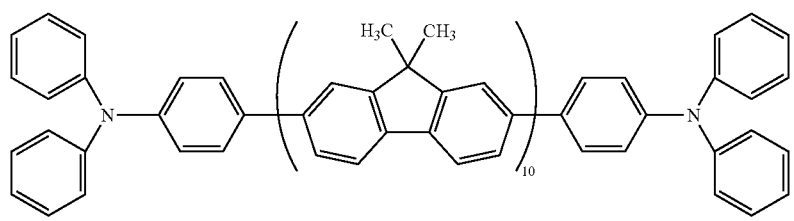
[XII]
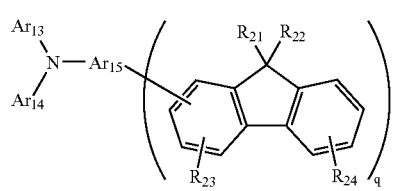
AA-47
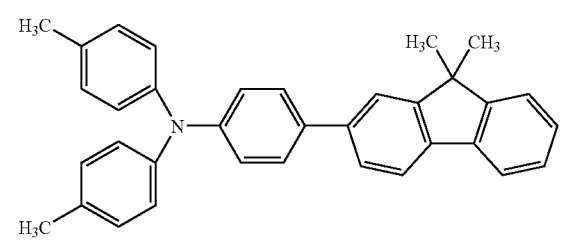

-continued
AA-48
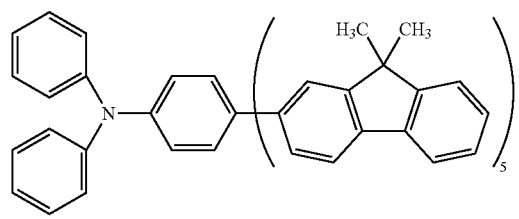
AA-49
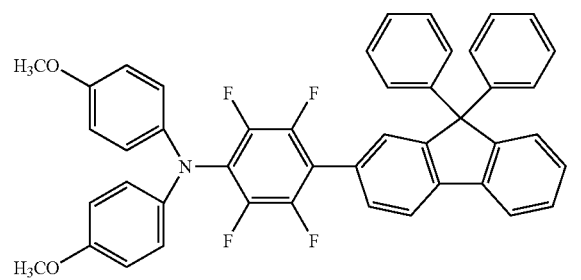
AA-50
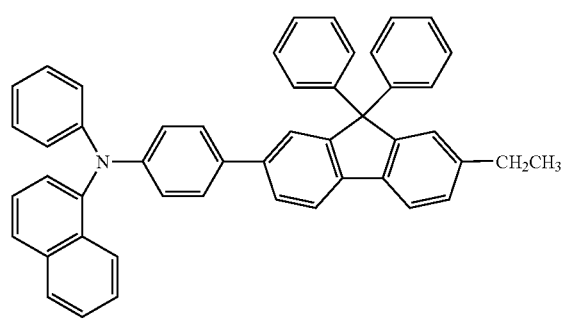
AA-51
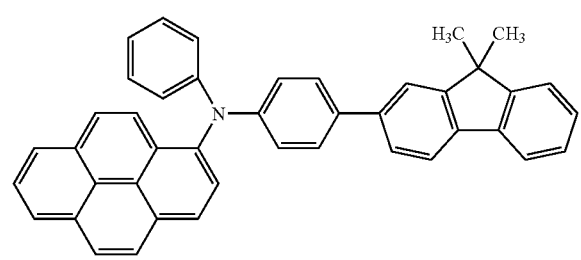
[XIII]
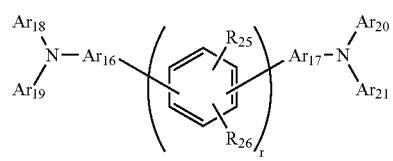
AA-52
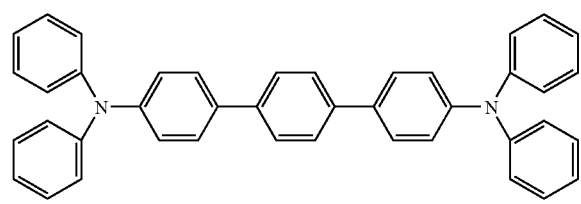
AA-53
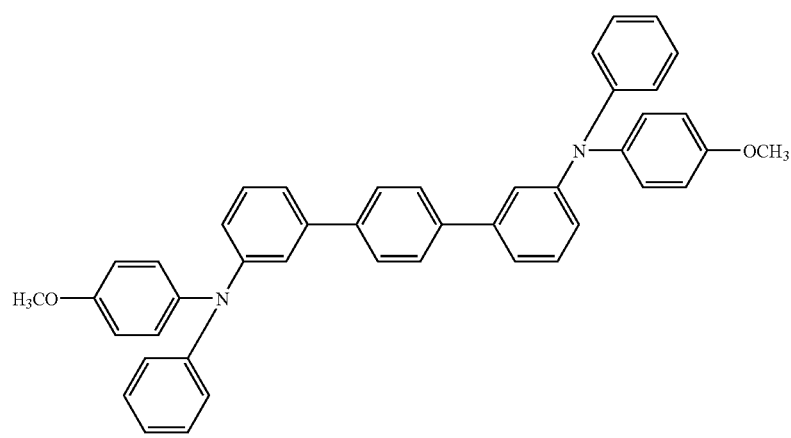
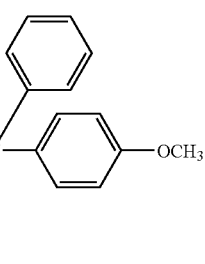
AA-54
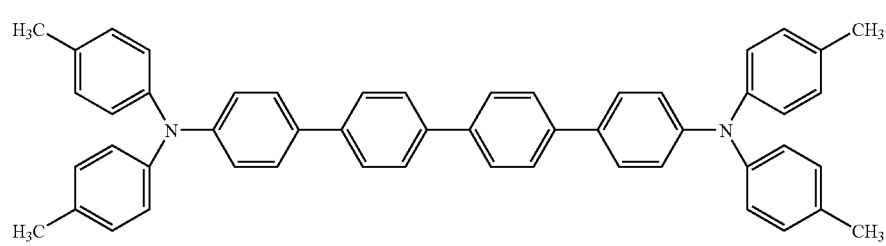

-continued
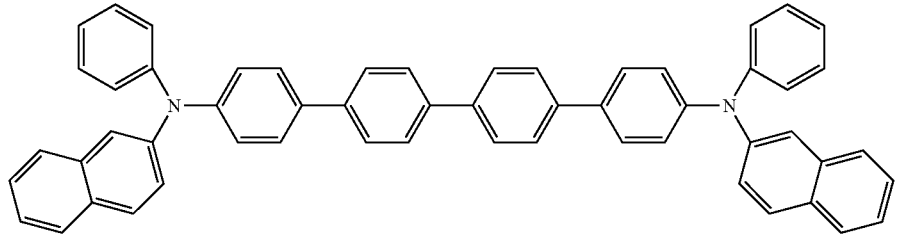
AA-55
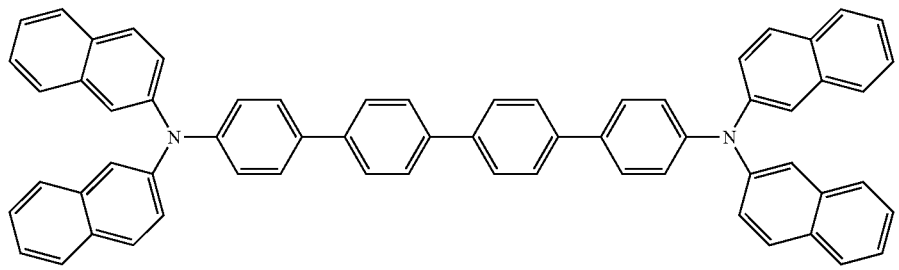
AA-56
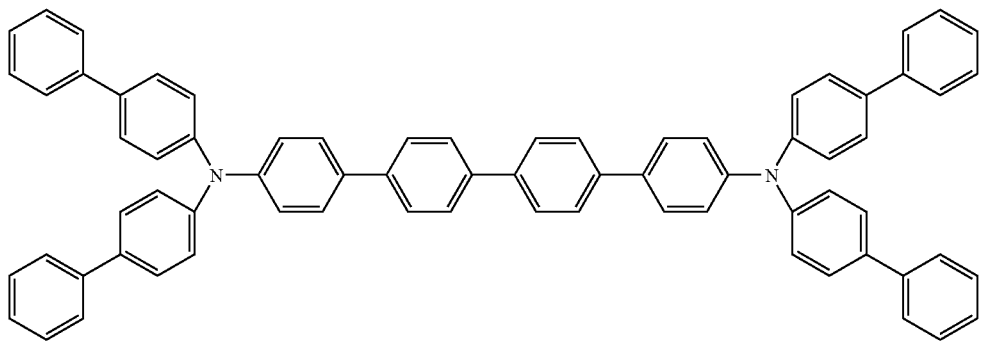
AA-57
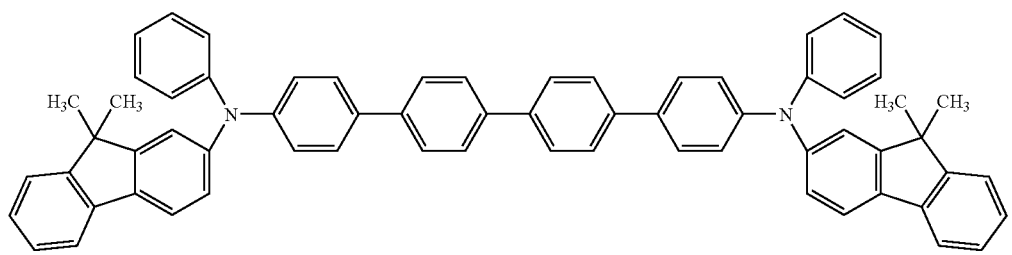
AA-58
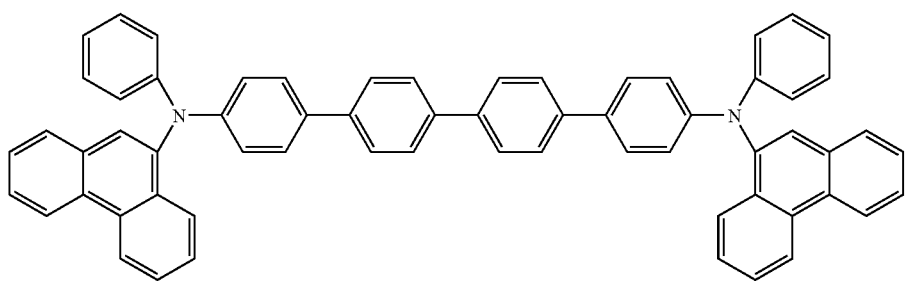
AA-59

-continued
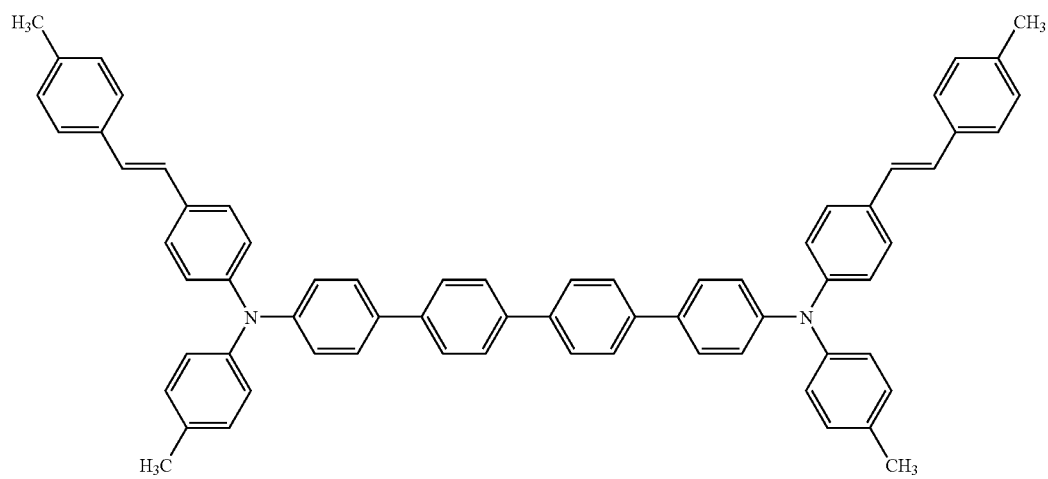
AA-60
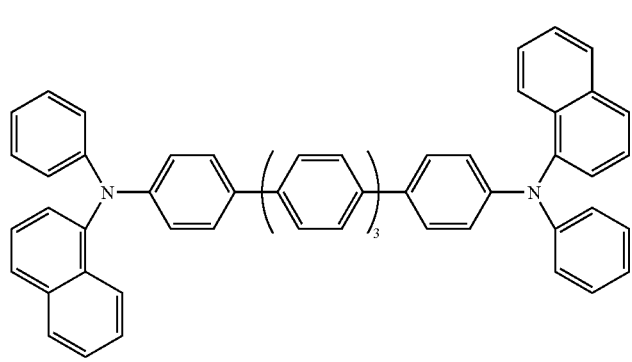
AA-61
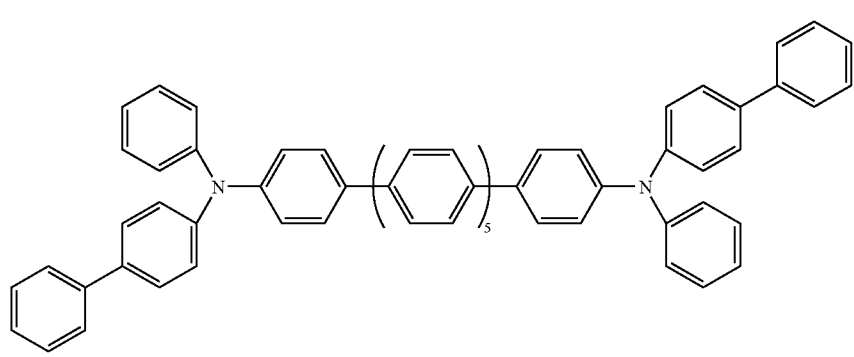
AA-62
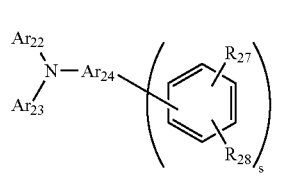
[XIV]
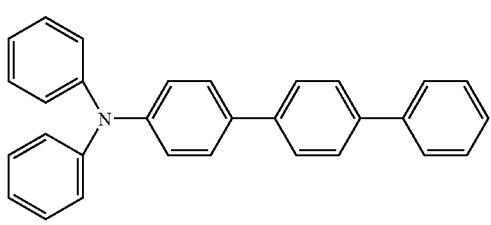
AA-63

-continued
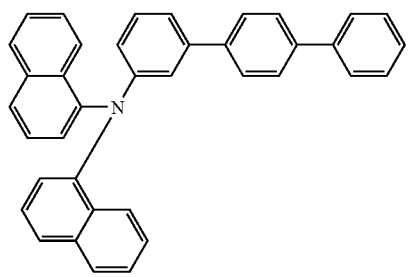 AA-64
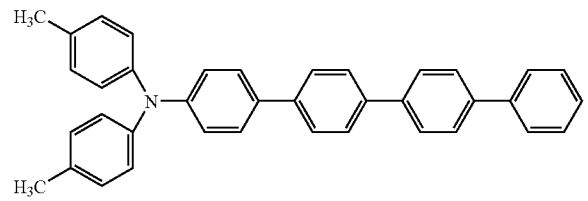 AA-65
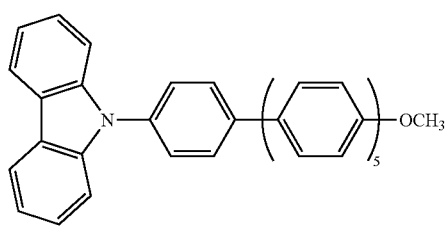 AA-66
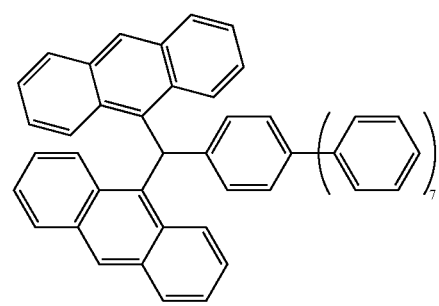 AA-67
$Ar_{25}\!-\!\!(C\!\equiv\!C)_{t}\!-\!Ar_{26}$ [XV]
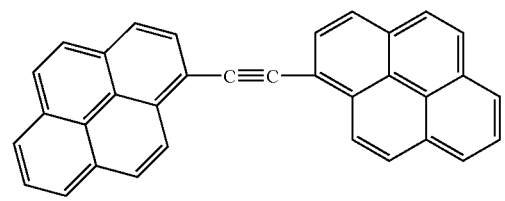 AC-68
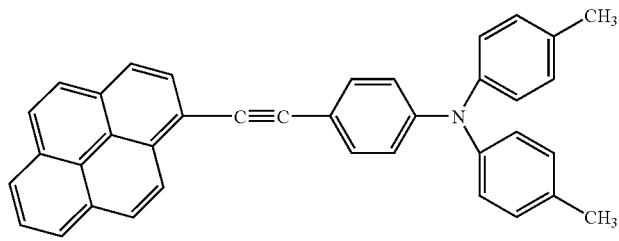 AC-69
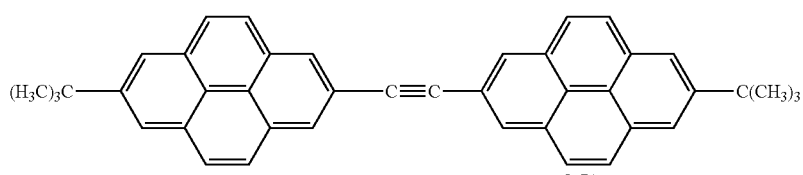 AC-70
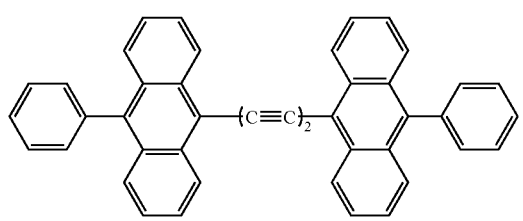 AC-71
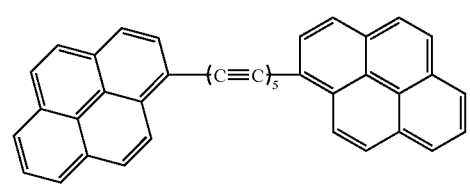 AC-72

In FIGS. 1 to 6, preferable examples of the organic luminescent device of the present invention are shown.

FIG. 1 is a cross-sectional view showing an example of the organic luminescent device of the present invention. In FIG. 1, the device is composed of an anode 2, a luminescent layer 3, and a cathode 4, which are formed on a substrate 1 in order. The luminescent device with this structure is advantageous when the luminescent material used herein has a hole-transporting ability, an electron-transporting ability, and a luminescence property in itself or when plural compounds having the respective characteristics are used as mixed.

Figure 2:
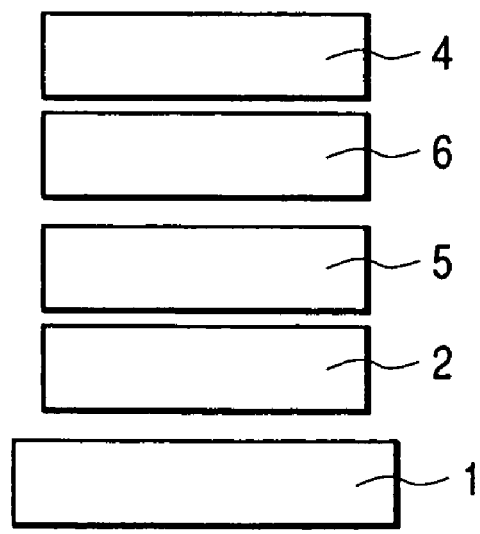
FIG. 2 is a cross-sectional view showing another example of the organic luminescent device in accordance with the present invention.

FIG. 2 is a cross-sectional view showing another example of the organic luminescent device of the present invention. In FIG. 2, the device is composed of an anode 2, a hole transport layer 5, an electron transport layer 6, and a cathode 4, which are formed on a substrate 1 in order. In this case, a luminescent material having either or both of a hole transport property and an electron transport property is advantageously used for the corresponding one of the layers, in combination with a hole transport material or an electron transport material having no luminescence property for the other layer. In addition, in this case, the luminescent layer 3 is composed of either the hole transport layer 5 or the electron transport layer 6.

Figure 3:
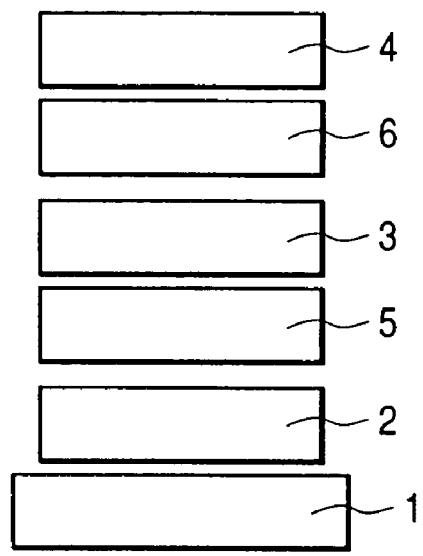
FIG. 3 is a cross-sectional view showing still another example of the organic luminescent device in accordance with the present invention.

FIG. 3 is a cross-sectional view showing still another example of the organic luminescent device of the present invention. In FIG. 3, the device is composed of an anode 2, a hole transport layer 5, a luminescent layer 3, an electron transport layer 6, and a cathode 4, which are formed on a substrate 1 in order. With this arrangement, a carrier transport function and a luminescence function are separated from each other, and plural compounds respectively having a hole transport property, an electron transport property, and a luminescence property are used appropriately in combination therewith. Thus, the degree of freedom upon selecting materials extremely increases. In addition, various kinds of compounds having different luminous wavelengths can be used. Therefore, a variety of luminescence hues can be achieved. Furthermore, it also becomes possible to increase the luminous efficiency by effectively confining each carrier or exciton in the middle luminescent layer 3.

Figure 4:
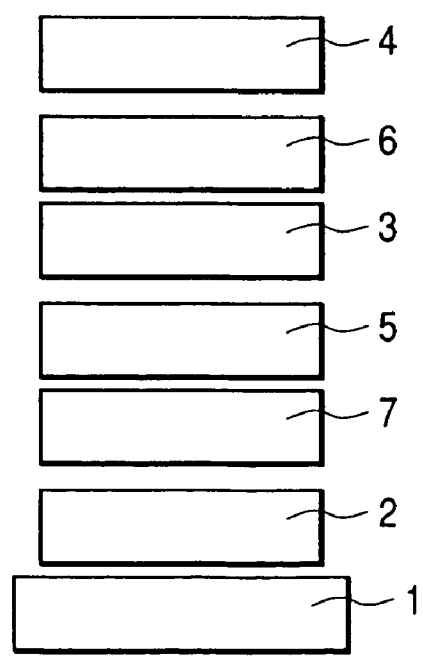
FIG. 4 is a cross-sectional view showing still another example of the organic luminescent device in accordance with the present invention.

FIG. 4 is a cross-sectional view showing still another example of the organic luminescent device of the present invention. In FIG. 4, as compared with the example of FIG. 3, the device is constructed such that a hole injecting layer 7 is inserted on the anode 2 side. It is effective for improving an adhesion between the anode 2 and the hole transport layer 5 or improving a hole injection property. Thus, this arrangement is effective for lowering a voltage.

Figure 5:
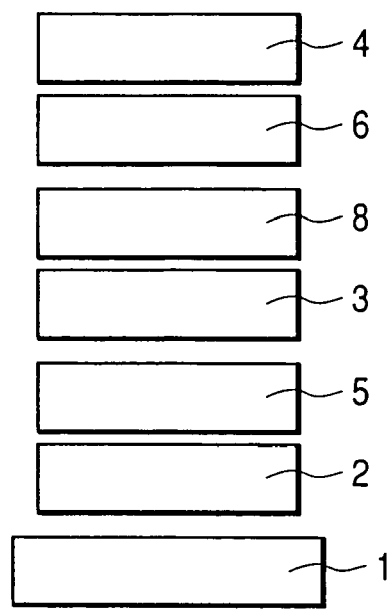
FIG. 5 is a cross-sectional view showing still another example of the organic luminescent device in accordance with the present invention.
Figure 6:
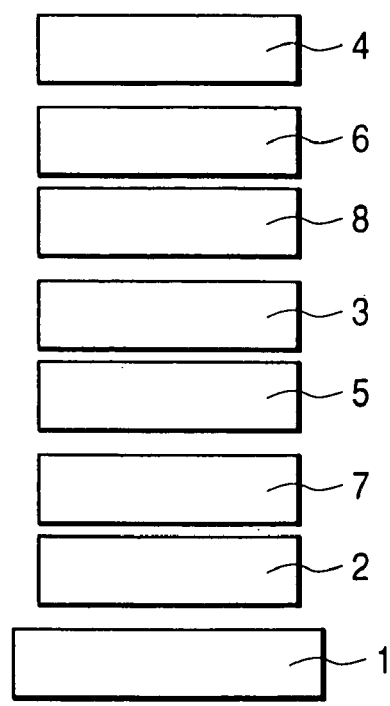
FIG. 6 is a cross-sectional view showing still another example of the organic luminescent device in accordance with the present invention.

FIGS. 5 and 6 are cross-sectional views showing other examples of the organic luminescent device of the present invention, respectively. In FIGS. 5 and 6, as compared with the examples of FIGS. 3 and 4, the device is constructed such that a layer (a hole-blocking layer 8) serving to prevent a hole or an exciton from passing toward the cathode 4 side is inserted between the luminescent layer 3 and the electron transport layer 6. The use of a compound having an extremely high ionization potential for the hole-blocking layer 8 is effective for improving the luminous efficiency.

Note that, in FIGS. 1 to 6, there are shown common basic device structures. The structure of the organic luminescent device using the compound of the present invention is not limited thereto. For example, it is possible to adopt various layer structures such as one in which an insulating layer is formed at the interface between an electrode and an organic layer, one in which an adhesive layer or an interference layer is formed, and one in which the hole transport layer is composed of two layers with different ionization potentials.

The fluorene compound represented by the general formula [I] to be used in the present invention is a compound superior to the conventional compounds in electron transport property, luminescence property, and durability, and the fluorene compound can be used in any of the modes shown in FIGS. 1 to 6.

In the present invention, the fluorene compound represented by the general formula [I] is used as a component for the electron transport layer or the luminescent layer. However, hole transport compounds, luminescent compounds, electron transport compounds, or other such well-known compounds may be used together as needed.

Examples of those compounds will be given below. Hole transport compound:

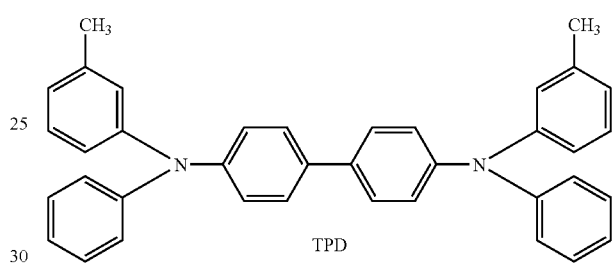

TPD

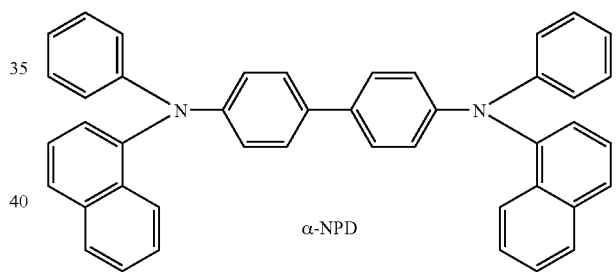

α-NPD

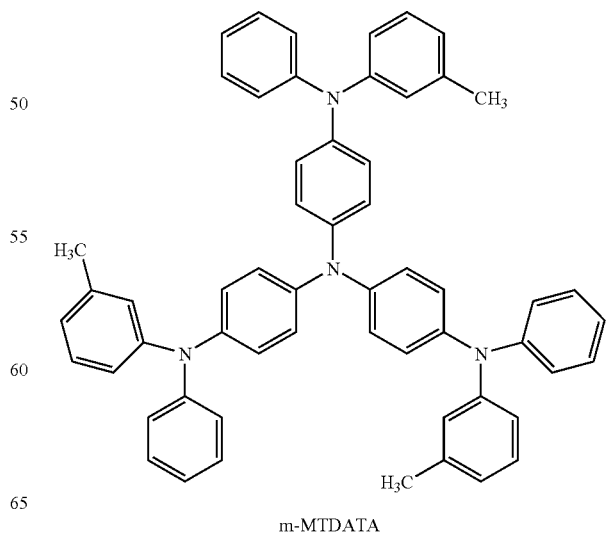

m-MTDATA

-continued
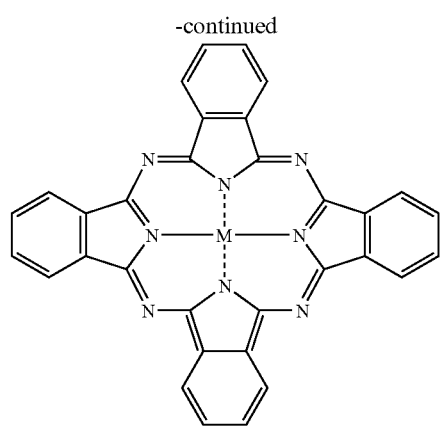
Pc—M
M: Cu, Mg, AlCl, TiO, SiCl₂, Zn, Sn, MnCl, GaCl, etc
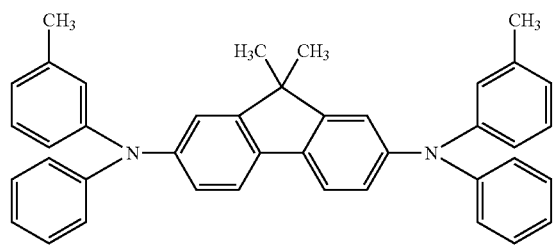
DTDPFL
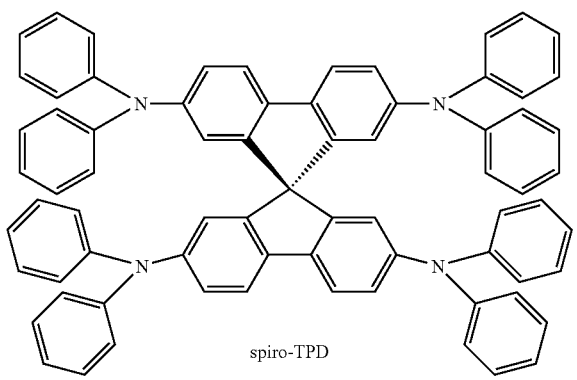
spiro-TPD
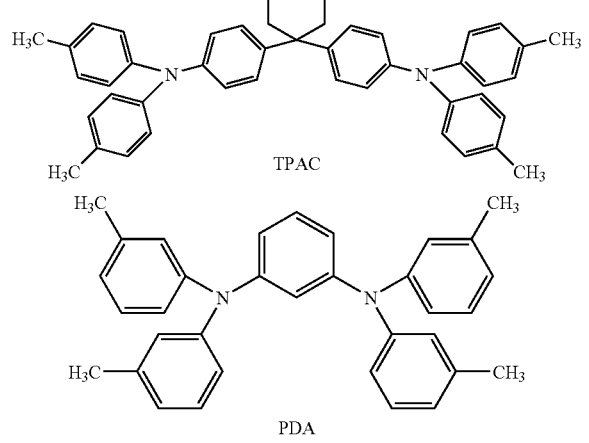
TPAC
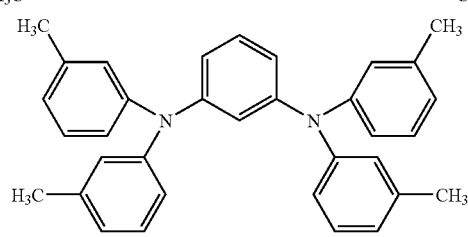
PDA
Electron Transport Luminescent Material:
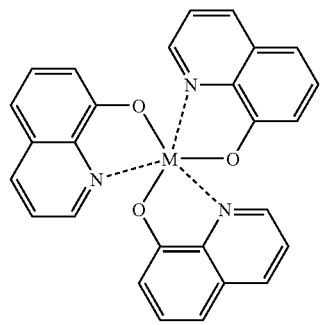
M: Al, Ga
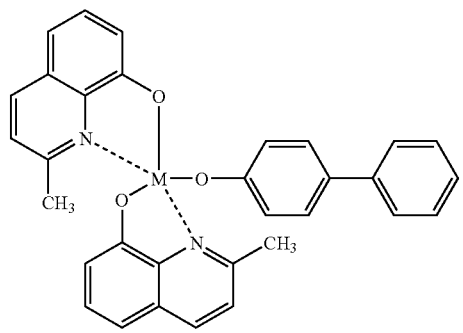
M: Al, Ga
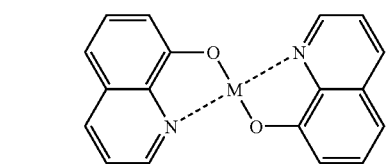
M: Zn, Mg, Be
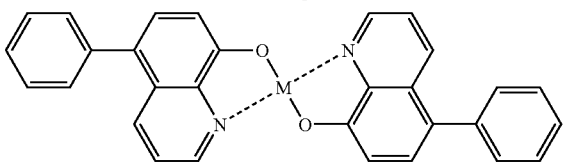
M: Zn, Mg, Be
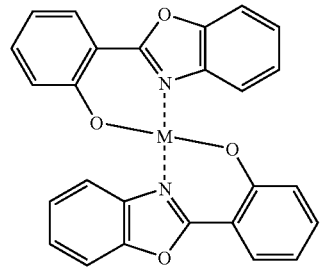
M: Zn, Mg, Be -continued
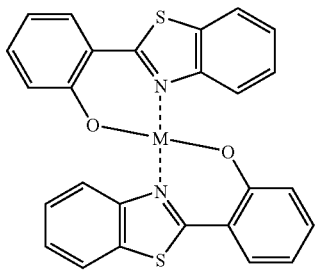
M: Zn, Mg, Be
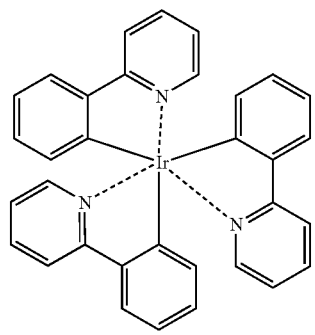
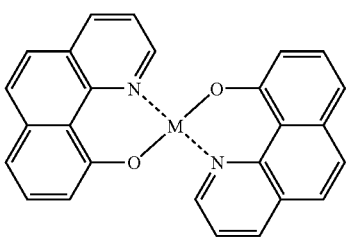
M: Zn, Mg, Be
-continued
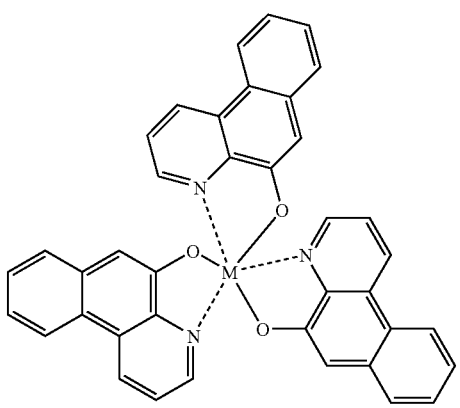
M: Al, Ga
Luminescent Material:
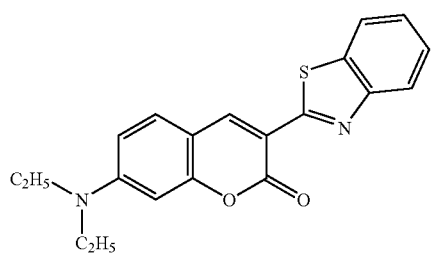
Coumarin 6
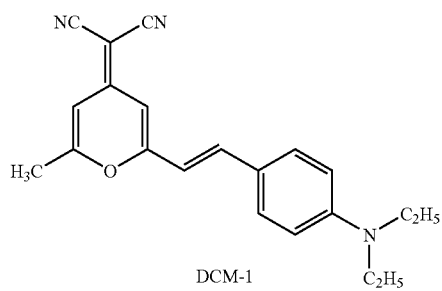
DCM-1
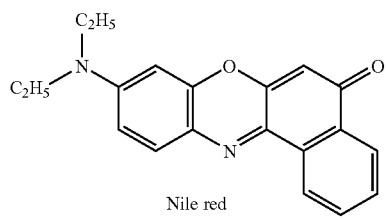
Nile red
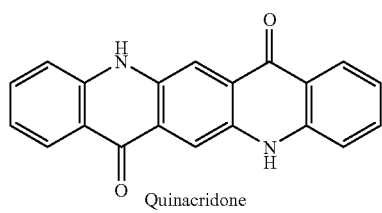
Quinacridone

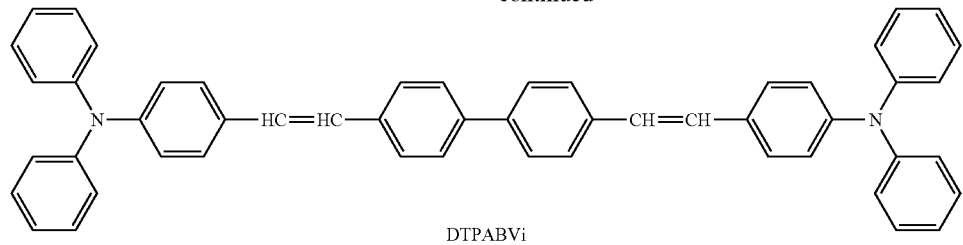
DTPABVi
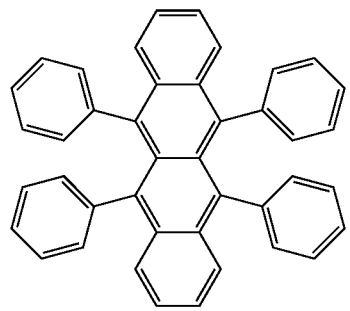
Rubrene
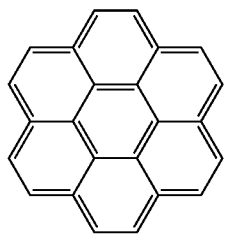
Coronene
Luminescent Layer Matrix Material and Electron Transport Material:
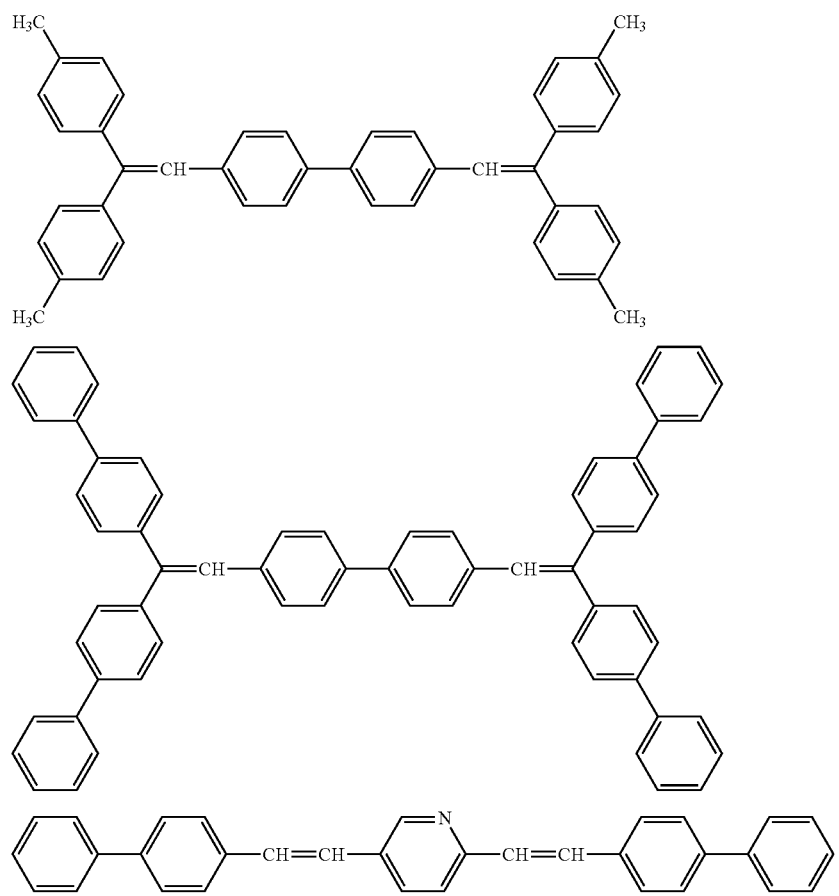

-continued
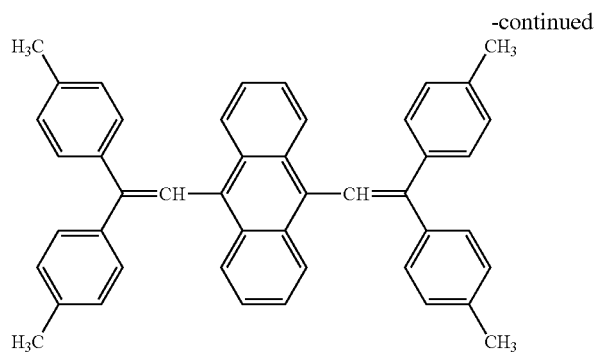
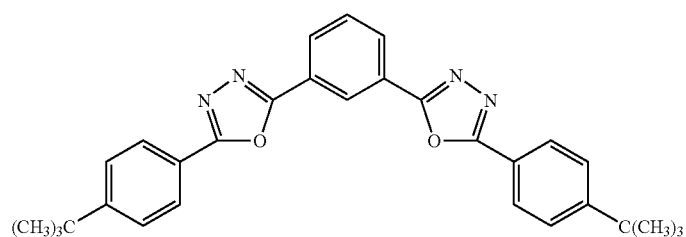
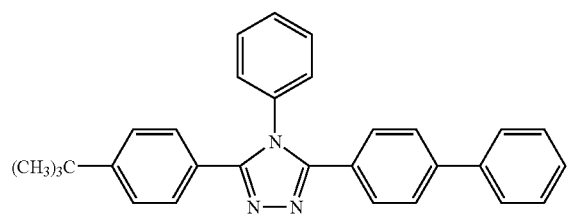
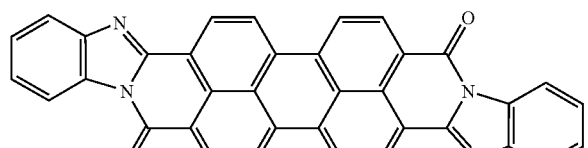
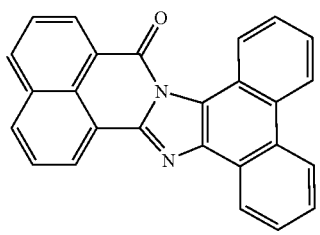
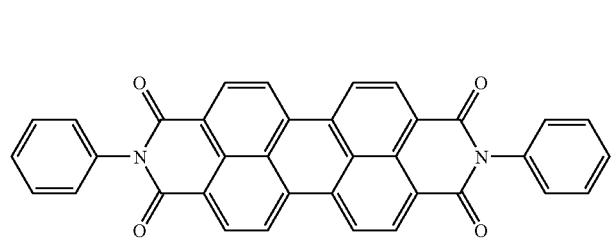
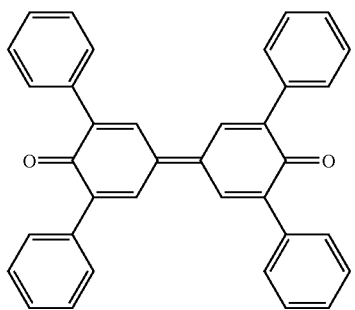

Polymeric Hole Transport Material:
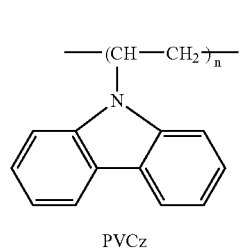
PVCz
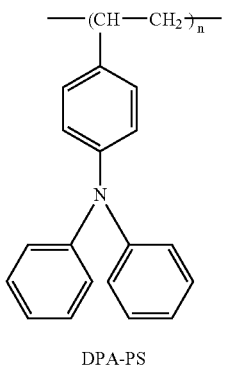
DPA-PS
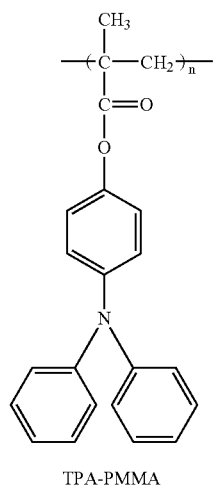
TPA-PMMA
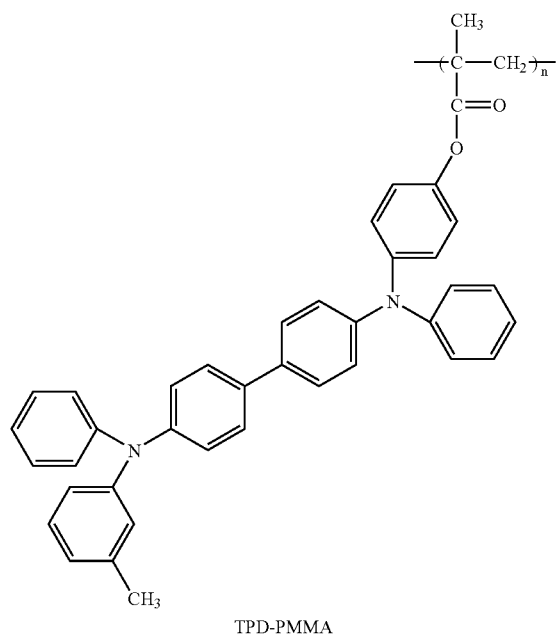
TPD-PMMA
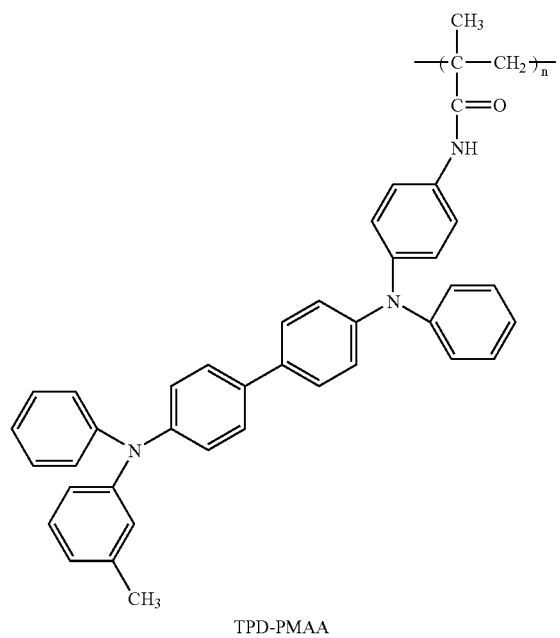
TPD-PMAA
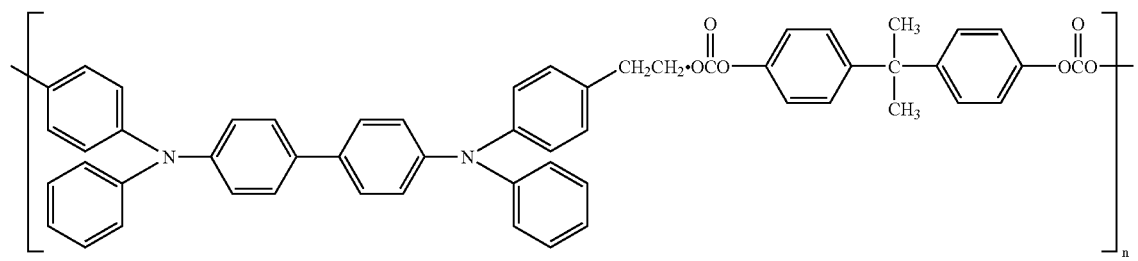
TPD-PCA

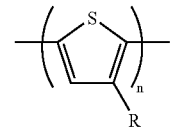

R: $C_6H_{13}$, $C_8H_{17}$, $C_{12}H_{25}$
Polythiophene

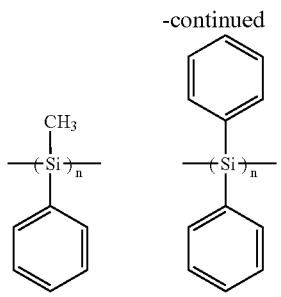

Polysilane

Polymeric Luminescent Material and Charge Transport Material:

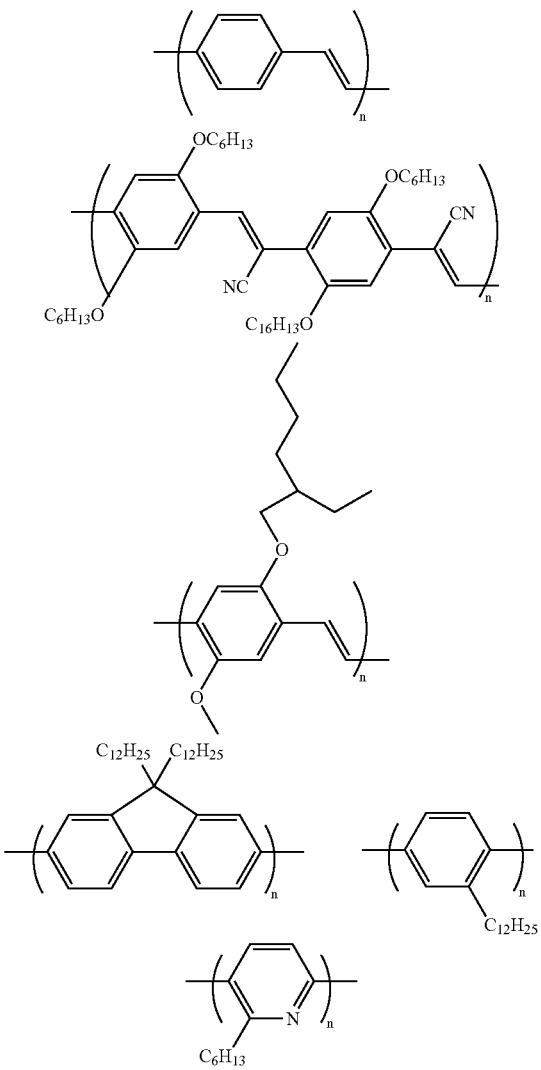

In the organic luminescent device of the present invention, the layer containing the fluorene compound represented by the general formula [I] and the layer containing other organic compounds are generally formed as thin films by a vacuum evaporation method or by a coating method after being dissolved in an appropriate solvent. In particular, in the case of forming a film with the coating method, the film formation may be performed in combination with an appropriate binder resin.

The above binder resin can be selected from a wide variety of binder resins including, for example, poly(vinylcarbazole) resin, polycarbonate resin, polyester resin, polyarylate resin, polystyrene resin, acrylic resin, methacrylic resin, butyral resin, poly(vinyl acetal) resin, diallyl phthalate resin, phenolic resin, epoxy resin, silicone resin, polysulfone resin, and urea resin, although not limited thereto. In addition, one of the above resins may be used solely, or two or more such resins may be combined with each other as a copolymer.

Preferably, the anode material may have a work function that is as large as possible. For example, a simple metal substance such as gold, platinum, nickel, palladium, cobalt, selenium, or vanadium, or an alloy thereof, or a metal oxide such as tin oxide, zinc oxide, indium tin oxide (ITO), or indium zinc oxide can be used. In addition, a conductive polymer such as polyaniline, polypyrrole, polythiophene, or poly(phenylene sulfide) can be also used. Any one of those electrode materials may be used solely or the plural electrode materials may be used in combination.

On the other hand, preferably, the cathode material may have a small work function. For example, a simple metal substance such as lithium, sodium, potassium, cesium, calcium, magnesium, aluminum, indium, silver, lead, tin, or chromium, or an alloy of the plural substances can be used therefor. It is also possible to use a metal oxide such as indium tin oxide (ITO). In addition, the cathode may take either a single-layer structure or a multi-layer structure.

The substrate used in the present invention may be, although not particularly limited, an untransparent substrate such as a metallic substrate or a ceramic substrate, or a transparent substrate formed of glass, quartz, plastic sheet, or the like. In addition, it is also possible to control the luminescent color by using a color filter film, a fluorescent color-converting filter film, a dielectric reflection film, or the like for the substrate.

Furthermore, a protective layer or a sealing layer may be also formed on the prepared device for preventing the device from contacting oxygen, moisture, or the like. The protective layer may be a diamond thin film, a film made of an inorganic material such as a metal oxide or a metal nitride, or a polymer film made of fluoroplastics, poly(paraxylylene), polyethylene, silicone resin, polystyrene resin, or the like. In addition, a photo-curing resin or the like can be used therefor. Furthermore, it is also possible to package the device itself with an appropriate sealing resin while covering with glass, a gas-impermeable film, a metal, or the like.

Hereinafter, the present invention will be described in more detail based on examples. However, the present invention is not limited to those examples.

Synthesis Example 1

Synthesis of Exemplified Compound No. 1

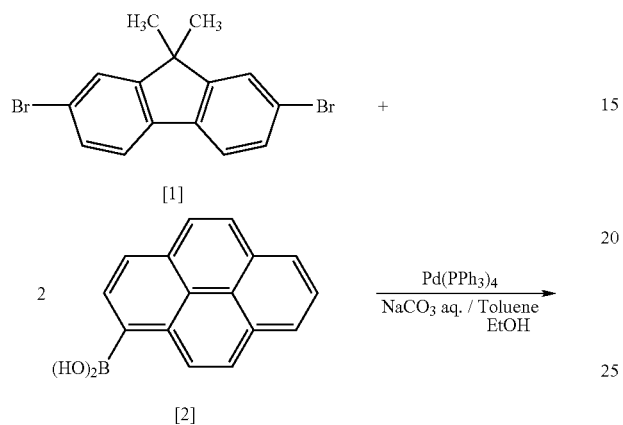

To a 500-ml three-neck flask, 2.0 g (5.68 mmol) of 2,7-dibromo-9,9-dimethylfluorene [1], 4.2 g (17.0 mmol) of pyrene-1-boronic acid [2], 120 ml of toluene, and 60 ml of ethanol were added. Then, an aqueous solution of 24 g of sodium carbonate/120 ml of water was dropped thereinto with stirring in a nitrogen atmosphere at a room temperature, followed by the addition of 0.33 g (0.28 mmol) of tetrakis (triphenylphosphine) palladium (0). After stirring the mixture for 30 minutes at a room temperature, the temperature was allowed to rise to 77° C., followed by stirring for 5 hours. After the reaction, an organic layer was extracted with chloroform and was then dried with anhydrous sodium sulfate, followed by purification with a silica gel column (hexane+toluene mixture developing solvent). Consequently, 3.0 g (89% yield) of an exemplified compound No. 1 (white crystal) was obtained.

Synthesis Example 2

Synthesis of Exemplified Compound No. 6

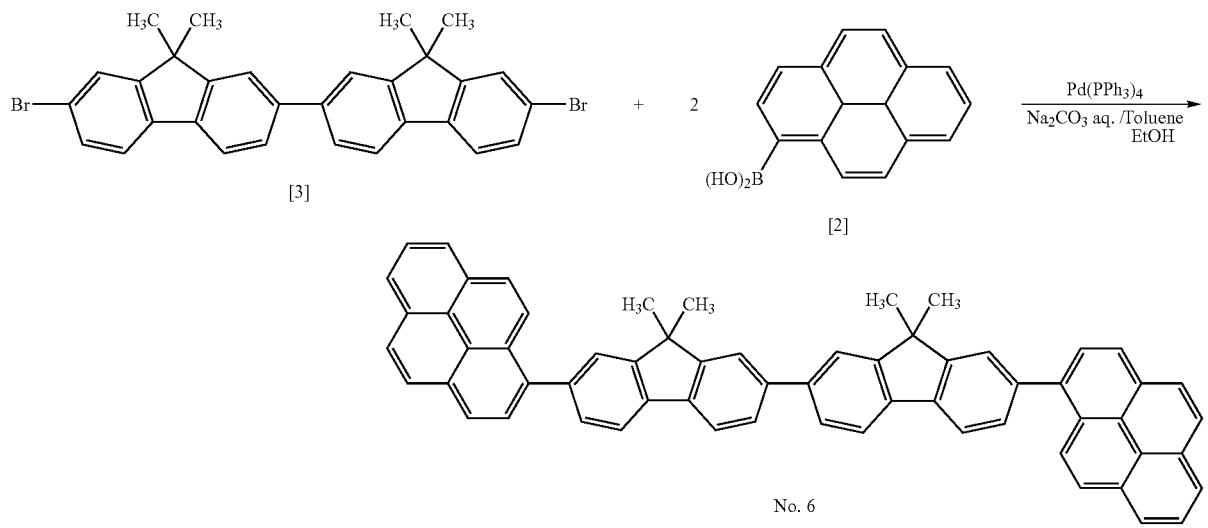

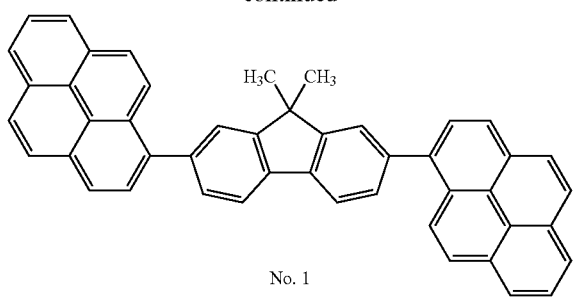

To a 500-ml three-neck flask, 3.0 g (5.49 mmol) of dibromofluorene compound [3], 4.0 g (16.5 mmol) of pyrene-1-boronic acid [2], 100 ml of toluene, and 50 ml of ethanol were added. Then, an aqueous solution of 20 g of sodium carbonate/100 ml of water was dropped thereinto with stirring in a nitrogen atmosphere at a room temperature, followed by the addition of 0.33 g (0.28 mmol) of tetrakis (triphenylphosphine) palladium (0). After stirring the mixture for 30 minutes at a room temperature, the temperature was allowed to rise to 77° C., followed by stirring for 5 hours. After the reaction, an organic layer was extracted with chloroform and was then dried with anhydrous sodium sulfate, followed by purification with a silica gel column (hexane+toluene mixture developing solvent). Consequently, 3.4 g (79% yield) of an exemplified compound No. 6 (white crystal) was obtained.

Synthesis Example 3

Synthesis of Exemplified Compound No. 7

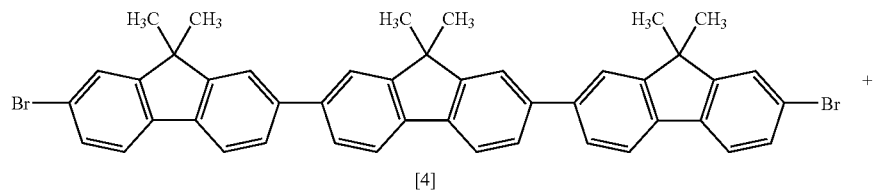

[4]

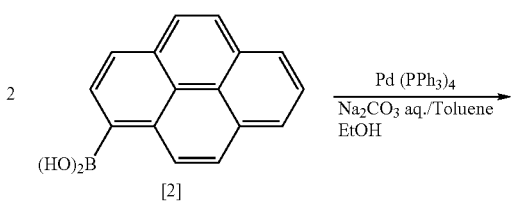

[2]

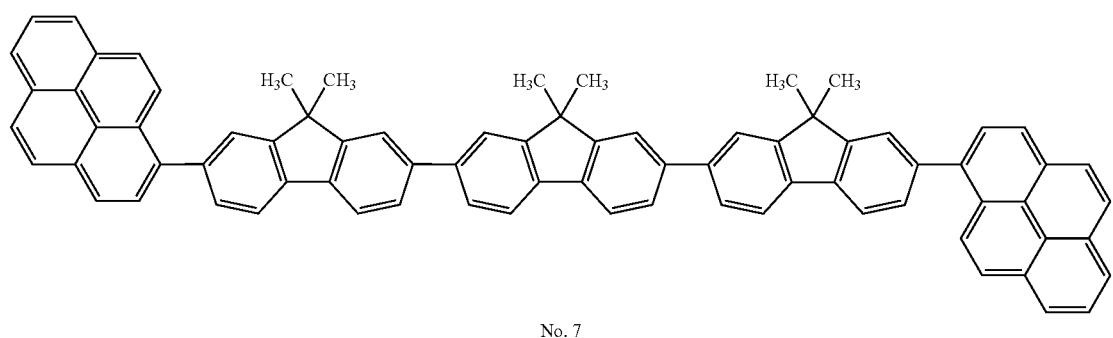

No. 7

To a 500-ml three-neck flask, 3.0 g (4.07 mmol) of dibromofluorene compound [4], 3.0 g (12.2 mmol) of pyrene-1-boronic acid [2], 100 ml of toluene, and 50 ml of ethanol were added. Then, an aqueous solution of 16 g of sodium carbonate/80 ml of water was dropped thereinto with stirring in a nitrogen atmosphere at a room temperature, followed by the addition of 0.23 g (0.20 mmol) of tetrakis (triphenylphosphine) palladium (0). After stirring the mixture for 30 minutes at a room temperature, the temperature was allowed to rise to 77° C., followed by stirring for 5 hours. After the reaction, an organic layer was extracted with chloroform and was then dried with anhydrous sodium sulfate, followed by purification with a silica gel column (hexane+toluene mixture developing solvent). Consequently, 2.7 g (68% yield) of an exemplified compound No. 7 (white crystal) was obtained.

Synthesis Example 4

Synthesis of Exemplified Compound No. 28

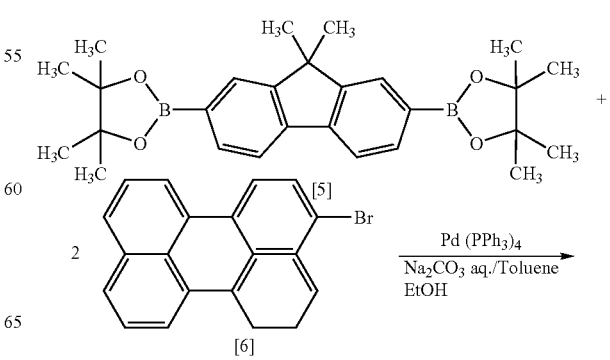

-continued

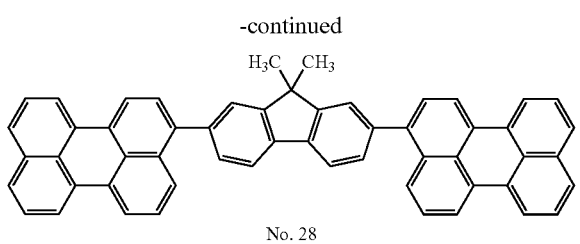

No. 28

To a 500-ml three-neck flask, 3.0 g (6.74 mmol) of diborate fluorene [5], 6.7 g (20.2 mmol) of 3-bromoperylene [6], 140 ml of toluene, and 70 ml of ethanol were added. Then, an aqueous solution of 26 g of sodium carbonate/130 ml of water was dropped thereinto with stirring at a room temperature in a nitrogen atmosphere, followed by the addition of 0.39 g (0.34 mmol) of tetrakis (triphenylphosphine) palladium (0). After stirring the mixture for 30 minutes at a room temperature, the temperature was allowed to rise to 77° C., followed by stirring for 10 hours. After the reaction, an organic layer was extracted with chloroform and was then dried with anhydrous sodium sulfate, followed by purification with a silica gel column (hexane+toluene mixture developing solvent). Consequently, 3.1 g (66% yield) of an exemplified compound No. 28 (white crystal) was obtained.

EXAMPLE 1

A device having the structure shown in FIG. 2 was prepared.

On a glass substrate as the substrate 1, indium tin oxide (ITO) was deposited into a film with a thickness of 120 nm by a sputtering method to obtain the anode 2, so that the substrate thus formed was used as a transparent conductive support substrate. The substrate was sequentially subjected to ultrasonic cleaning with acetone and with isopropyl alcohol (IPA). Following this, the substrate was washed with IPA through boiling and then dried. Furthermore, the substrate after UV/ozone cleaning was used as the transparent conductive support substrate.

On the transparent conductive support substrate, a chloroform solution of the compound represented by the following structural formula was applied to form a film of 30 nm in thickness by a spin-coating method, resulting in the hole transport layer 5.

Furthermore, a fluorene compound represented as the exemplified compound No. 1 was deposited into a film of 50 nm in thickness by a vacuum evaporation method, resulting in the electron transport layer 6. The film formation was performed under the conditions that the degree of vacuum at the time of evaporation was $1.0\times10^{-4}$ Pa and the film formation rate was 0.2 to 0.3 nm/sec.

A metal layer film of 50 nm in thickness was formed on the above organic layer as the cathode 4 using an evaporation material including aluminum and lithium (lithium concentration: 1% by atom) by a vacuum evaporation method, and further an aluminum layer of 150 nm in thickness was formed by a vacuum evaporation method. The film formation was performed under the conditions that the degree of vacuum at the time of evaporation was $1.0\times10^{-4}$ Pa and the film formation rate was 1.0 to 1.2 nm/sec.

Furthermore, the resultant structure was covered with a protective glass plate in a nitrogen atmosphere and was then sealed with an acrylic resin adhesive.

When a direct current voltage of 10 V was applied onto the device thus obtained with an ITO electrode (anode 2) provided as a positive electrode and an Al—Li electrode (cathode 4) provided as a negative electrode, electric current was caused to flow into the device at a current density of 12.5 mA/cm$^2$ and blue-colored luminescence at a luminance of 8500 cd/m$^2$ was observed.

Furthermore, when the current density was kept at 10.0 mA/cm$^2$ and the voltage was applied for 100 hours, the deterioration of luminance was small; an initial luminance of 7200 cd/m$^2$ was reduced to a luminance of 6800 cd/m$^2$ after 100 hours.

EXAMPLES 2 TO 10

Devices were prepared and evaluated in the same way as that of Example 1, except that compounds shown in Table 1 were used in place of the exemplified compound No. 1. The results are shown in Table 1.

Comparative Examples 1 to 3

Devices were prepared and evaluated in the same way as that of Example 1, except that compounds represented by the following structural formulae were used in place of the exemplified compound No. 1. The results are shown in Table 1.

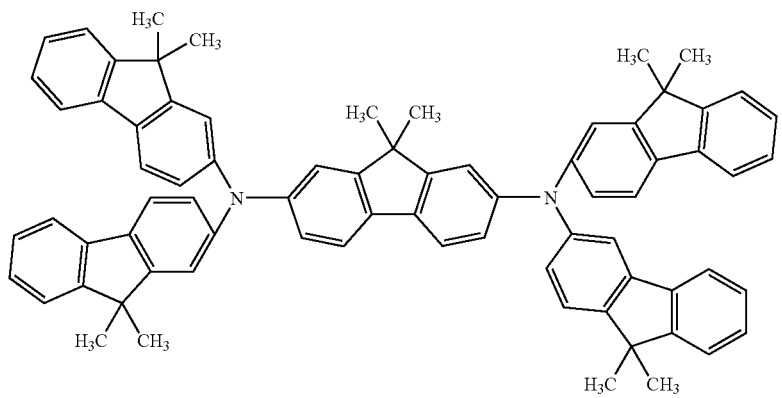

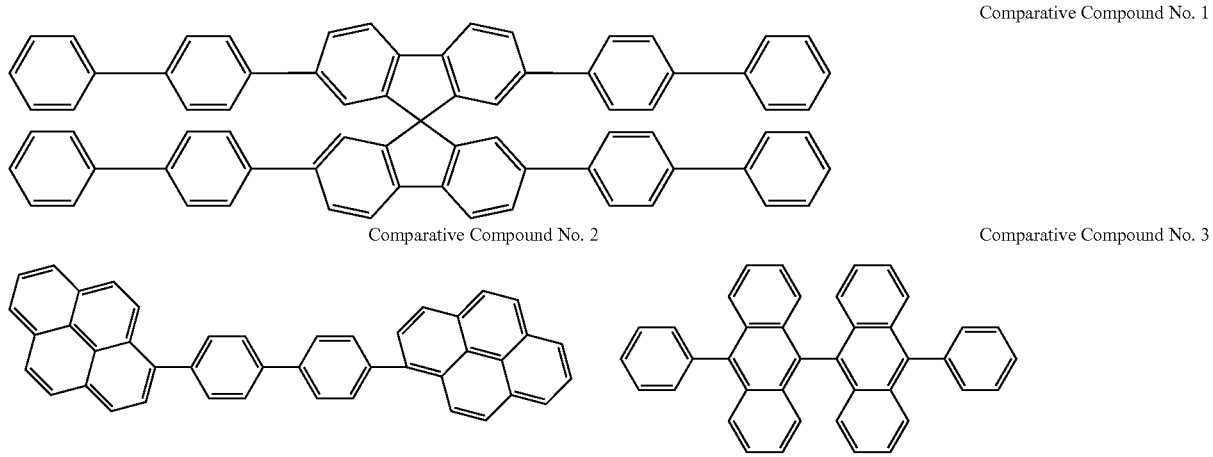

TABLE 1

| Example No. | Exemplified compound No. | Initial stage | | Durability | | |
|---|---|---|---|---|---|---|
| | | Applied voltage (V) | Luminance (cd/m$^2$) | Current density (mA/cm$^2$) | Initial luminance (cd/m$^2$) | Luminance after 100-hour (cd/m$^2$) |
| Example 1 | 1 | 10 | 8500 | 10.0 | 7200 | 6800 |
| Example 2 | 6 | 10 | 8800 | 10.0 | 7900 | 7600 |
| Example 3 | 13 | 10 | 4800 | 10.0 | 4300 | 4100 |
| Example 4 | 15 | 10 | 8200 | 10.0 | 7000 | 6700 |
| Example 5 | 22 | 10 | 5000 | 10.0 | 4500 | 4200 |
| Example 6 | 27 | 10 | 7400 | 10.0 | 7200 | 6900 |
| Example 7 | 29 | 10 | 8000 | 10.0 | 7100 | 6700 |
| Example 8 | 32 | 10 | 6600 | 10.0 | 5700 | 5500 |
| Example 9 | 35 | 10 | 6700 | 10.0 | 5600 | 5200 |
| Example 10 | 39 | 10 | 4700 | 10.0 | 4300 | 4000 |
| Comparative Example 1 | Comparative 1 | 10 | 900 | 10.0 | 750 | 400 |
| Comparative Example 2 | Comparative 2 | 10 | 750 | 10.0 | 700 | 200 |
| Comparative Example 3 | Comparative 3 | 10 | 1400 | 10.0 | 1100 | 500 |

EXAMPLE 11

A device having the structure shown in FIG. 3 was prepared.

Similarly to Example 1, the hole transport layer 5 was formed on the transparent conductive support substrate.

Further, a fluorene compound represented as an exemplified compound No. 2 was deposited into a film of 20 nm in thickness by a vacuum evaporation method, resulting in the luminescent layer 3. The film formation was performed under the conditions that the degree of vacuum at the time of evaporation was $1.0 \times 10^{-4}$ Pa and the film formation rate was 0.2 to 0.3 nm/sec.

Furthermore, aluminum tris quinolinol was deposited into a film of 40 nm in thickness by a vacuum evaporation method, resulting in the electron transport layer 6. The film formation was performed under the conditions that the degree of vacuum at the time of evaporation was $1.0 \times 10^{-4}$ Pa and the film formation rate was 0.2 to 0.3 nm/sec.

Next, after forming the cathode 4 in the same manner as in Example 1, the resultant structure was sealed.

When a direct current voltage of 8 V was applied onto the device thus obtained with the ITO electrode (anode 2) provided as a positive electrode and the Al—Li electrode (cathode 4) provided as a negative electrode, electric current was caused to flow into the device at a current density of 12.0 mA/cm$^2$ and blue-colored luminescence at a luminance of 16000 cd/m$^2$ was observed.

Furthermore, when the current density was kept at 10.0 mA/cm$^2$ and the voltage was applied for 100 hours, the deterioration of luminance was small; an initial luminance of 14000 cd/m$^2$ was reduced to a luminance of 13000 cd/m$^2$ after 100 hours.

EXAMPLES 12 TO 22

Devices were prepared and evaluated in the same way as that of Example 11, except that compounds shown in Table 2 were used in place of the exemplified compound No. 7. The results are shown in Table 2.

Comparative Examples 4 to 6

Devices were prepared and evaluated in the same way as that of Example 11, except that comparative compounds No. 1 to No. 3 were used in place of the exemplified compound No. 7. The results are shown in Table 2.

TABLE 2

| | | Initial stage | | Durability | | |
|---|---|---|---|---|---|---|
| Example No. | Exemplified compound No. | Applied voltage (V) | Luminance (cd/m²) | Current density (mA/cm²) | Initial luminance (cd/m²) | Luminance after 100-hour (cd/m²) |
| Example 11 | 2 | 8 | 16000 | 10.0 | 14000 | 13000 |
| Example 12 | 5 | 8 | 10000 | 10.0 | 9000 | 8000 |
| Example 13 | 7 | 8 | 14000 | 10.0 | 11000 | 9500 |
| Example 14 | 9 | 8 | 12000 | 10.0 | 10000 | 9000 |
| Example 15 | 11 | 8 | 13000 | 10.0 | 10000 | 8500 |
| Example 16 | 16 | 8 | 10000 | 10.0 | 8000 | 7000 |
| Example 17 | 21 | 8 | 8500 | 10.0 | 7500 | 7000 |
| Example 18 | 26 | 8 | 9000 | 10.0 | 8000 | 7000 |
| Example 19 | 30 | 8 | 9500 | 10.0 | 9000 | 8000 |
| Example 20 | 33 | 8 | 10000 | 10.0 | 9000 | 7500 |
| Example 21 | 37 | 8 | 10000 | 10.0 | 8500 | 8000 |
| Example 22 | 38 | 8 | 9000 | 10.0 | 8000 | 7000 |
| Comparative Example 4 | Comparative 1 | 8 | 2000 | 10.0 | 1500 | 900 |
| Comparative Example 5 | Comparative 2 | 8 | 1500 | 10.0 | 1000 | 300 |
| Comparative Example 6 | Comparative 3 | 8 | 3000 | 10.0 | 2500 | 1000 |

EXAMPLE 23

A device having the structure shown in FIG. 3 was prepared.

On the transparent conductive support substrate similar to that in Example 1, a chloroform solution of a compound represented by the following structural formula was applied to form a film of 20 nm in thickness by a spin-coating method, resulting in the hole transport layer 5.

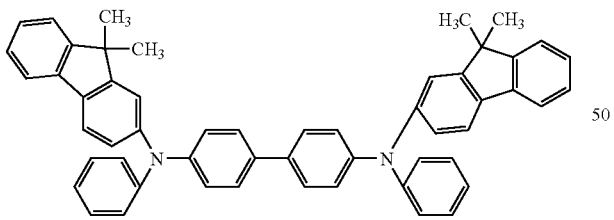

Furthermore, the fluorene compound represented as the exemplified compound No. 1 and the arylamine compound represented as an exemplified compound No. AA-6 (weight ratio of 100:1) were deposited into a film with a thickness of 20 nm by a vacuum evaporation method to form the luminescent layer 3. The film formation was performed under the conditions that the degree of vacuum at the time of evaporation was $1.0 \times 10^{-4}$ Pa and the film formation rate was 0.2 to 0.3 nm/sec.

Furthermore, aluminum tris quinolinol is deposited into a film of 40 nm in thickness by a vacuum evaporation method, resulting in the electron transport layer 6. The film formation was performed under the conditions that the degree of vacuum at the time of evaporation was $1.0 \times 10^{-4}$ Pa and the film formation rate was 0.2 to 0.3 nm/sec.

Next, after forming the cathode 4 in the same manner as in Example 1, the resultant structure was sealed. When a direct current voltage of 8 V was applied on the device thus obtained with an ITO electrode (anode 2) provided as a positive electrode and an Al—Li electrode (cathode 4) provided as a negative electrode, electric current was caused to flow into the device at a current density of 13.0 mA/cm² and blue-colored luminescence at a luminance of 32000 cd/m² was observed.

Furthermore, when the current density was kept at 10.0 mA/cm² and the voltage was applied for 100 hours, the deterioration of luminance was small; the initial luminance of 25000 cd/m² was reduced to a luminance of 22000 cd/m² after 100 hours.

EXAMPLES 24 TO 77

Devices were prepared and evaluated in the same way as that of Example 23, except that compounds shown in Tables 3 to 5 were used in place of the exemplified fluorene compound No. 1 and the exemplified arylamine compound No. AA-6, respectively. The results are shown in Tables 3 to 5.

Comparative Examples 7 to 9

Devices were prepared and evaluated in the same way as that of Example 23, except that the comparative compounds No. 1 to No. 3 were used in place of the exemplified compound No. 1. The results are shown in Table 5

TABLE 3

| Example No. | Exemplified compound No. | Exemplified arylamine compound No. | Applied voltage (V) | Initial stage Luminance (cd/m$^2$) | Current density (mA/cm$^2$) | Durability Initial luminance (cd/m$^2$) | Luminance after 100-hour (cd/m$^2$) |
|---|---|---|---|---|---|---|---|
| Example 23 | 1  | AA-6  | 8 | 32000 | 10.0 | 25000 | 22000 |
| Example 24 | 1  | AA-7  | 8 | 34000 | 10.0 | 28000 | 25000 |
| Example 25 | 1  | AA-10 | 8 | 35000 | 10.0 | 28000 | 24000 |
| Example 26 | 1  | AA-1  | 8 | 31000 | 10.0 | 24000 | 20000 |
| Example 27 | 1  | AA-2  | 8 | 31000 | 10.0 | 23000 | 20000 |
| Example 28 | 8  | AA-3  | 8 | 22000 | 10.0 | 19000 | 16000 |
| Example 29 | 10 | AA-4  | 8 | 24000 | 10.0 | 20000 | 17000 |
| Example 30 | 10 | AA-5  | 8 | 19000 | 10.0 | 17000 | 15000 |
| Example 31 | 10 | AA-12 | 8 | 23000 | 10.0 | 21000 | 17000 |
| Example 32 | 12 | AA-13 | 8 | 26000 | 10.0 | 22000 | 17000 |
| Example 33 | 1  | AA-14 | 8 | 32000 | 10.0 | 26000 | 21000 |
| Example 34 | 2  | AA-14 | 8 | 35000 | 10.0 | 27000 | 22000 |
| Example 35 | 1  | AA-15 | 8 | 34000 | 10.0 | 29000 | 25000 |
| Example 36 | 1  | AA-18 | 8 | 37000 | 10.0 | 31000 | 27000 |
| Example 37 | 1  | AA-21 | 8 | 35000 | 10.0 | 30000 | 25000 |
| Example 38 | 5  | AA-21 | 8 | 36000 | 10.0 | 29000 | 26000 |
| Example 39 | 1  | AA-24 | 8 | 38000 | 10.0 | 32000 | 28000 |
| Example 40 | 14 | AA-26 | 8 | 18000 | 10.0 | 17000 | 14000 |
| Example 41 | 1  | AA-27 | 8 | 30000 | 10.0 | 24000 | 21000 |

TABLE 4

| Example No. | Exemplified compound No. | Exemplified arylamine compound No. | Applied voltage (V) | Initial stage Luminance (cd/m$^2$) | Current density (mA/cm$^2$) | Durability Initial luminance (cd/m$^2$) | Luminance after 100-hour (cd/m$^2$) |
|---|---|---|---|---|---|---|---|
| Example 42 | 10 | AA-28 | 8 | 20000 | 10.0 | 18000 | 14000 |
| Example 43 | 10 | AA-29 | 8 | 16000 | 10.0 | 13000 | 10000 |
| Example 44 | 17 | AA-30 | 8 | 17000 | 10.0 | 15000 | 11000 |
| Example 45 | 18 | AA-31 | 8 | 22000 | 10.0 | 19000 | 17000 |
| Example 46 | 1  | AA-32 | 8 | 33000 | 10.0 | 27000 | 23000 |
| Example 47 | 1  | AA-33 | 8 | 34000 | 10.0 | 29000 | 25000 |
| Example 48 | 1  | AA-37 | 8 | 36000 | 10.0 | 31000 | 28000 |
| Example 49 | 1  | AA-38 | 8 | 31000 | 10.0 | 25000 | 21000 |
| Example 50 | 1  | AA-39 | 8 | 35000 | 10.0 | 30000 | 25000 |
| Example 51 | 8  | AA-44 | 8 | 23000 | 10.0 | 21000 | 18000 |
| Example 52 | 1  | AA-45 | 8 | 29000 | 10.0 | 23000 | 19000 |
| Example 53 | 19 | AA-46 | 8 | 29000 | 10.0 | 24000 | 19000 |
| Example 54 | 1  | AA-47 | 8 | 30000 | 10.0 | 24000 | 21000 |
| Example 55 | 1  | AA-48 | 8 | 27000 | 10.0 | 20000 | 16000 |
| Example 56 | 8  | AA-49 | 8 | 19000 | 10.0 | 16000 | 12000 |
| Example 57 | 10 | AA-50 | 8 | 25000 | 10.0 | 20000 | 15000 |
| Example 58 | 10 | AA-51 | 8 | 24000 | 10.0 | 20000 | 17000 |
| Example 59 | 1  | AA-52 | 8 | 30000 | 10.0 | 25000 | 22000 |
| Example 60 | 28 | AA-53 | 8 | 19000 | 10.0 | 14000 | 10000 |

TABLE 5

| Example No. | Exemplified compound No. | Exemplified arylamine compound No. | Applied voltage (V) | Initial stage Luminance (cd/m$^2$) | Current density (mA/cm$^2$) | Durability Initial luminance (cd/m$^2$) | Luminance after 100-hour (cd/m$^2$) |
|---|---|---|---|---|---|---|---|
| Example 61 | 1  | AA-54 | 8 | 31000 | 10.0 | 25000 | 23000 |
| Example 62 | 1  | AA-55 | 8 | 32000 | 10.0 | 27000 | 25000 |
| Example 63 | 1  | AA-58 | 8 | 31000 | 10.0 | 24000 | 22000 |
| Example 64 | 2  | AA-58 | 8 | 33000 | 10.0 | 27000 | 23000 |
| Example 65 | 5  | AA-55 | 8 | 30000 | 10.0 | 25000 | 22000 |
| Example 66 | 28 | AA-61 | 8 | 25000 | 10.0 | 22000 | 17000 |
| Example 67 | 1  | AA-62 | 8 | 27000 | 10.0 | 23000 | 20000 |
| Example 68 | 1  | AA-63 | 8 | 29000 | 10.0 | 23000 | 20000 |
| Example 69 | 1  | AA-64 | 8 | 27000 | 10.0 | 20000 | 18000 |
| Example 70 | 1  | AA-65 | 8 | 30000 | 10.0 | 24000 | 20000 |

TABLE 5-continued

| | | Initial stage | | Durability | | |
|---|---|---|---|---|---|---|
| Example No. | Examplified compound No. | Exemplified arylamine compound No. | Applied voltage (V) | Luminance (cd/m$^2$) | Current density (mA/cm$^2$) | Initial luminance (cd/m$^2$) | Luminance after 100-hour (cd/m$^2$) |
| Example 71 | 31 | AA-66 | 8 | 18000 | 10.0 | 15000 | 10000 |
| Example 72 | 10 | AA-67 | 8 | 16000 | 10.0 | 14000 | 9000 |
| Example 73 | 1 | AC-68 | 8 | 31000 | 10.0 | 26000 | 22000 |
| Example 74 | 1 | AC-69 | 8 | 28000 | 10.0 | 22000 | 18000 |
| Example 75 | 1 | AC-70 | 8 | 30000 | 10.0 | 23000 | 18000 |
| Example 76 | 28 | AC-71 | 8 | 21000 | 10.0 | 18000 | 14000 |
| Example 77 | 28 | AC-72 | 8 | 23000 | 10.0 | 20000 | 16000 |
| Comparative Example 7 | Comparative 1 | AA-6 | 8 | 5000 | 10.0 | 4000 | 1500 |
| Comparative Example 8 | Comparative 2 | AA-6 | 8 | 3500 | 10.0 | 2500 | 900 |
| Comparative Example 9 | Comparative 3 | AA-6 | 8 | 6000 | 10.0 | 4000 | 1000 |

EXAMPLE 78

A device having the structure shown in FIG. 3 was prepared.

On the transparent conductive support substrate similar to that in Example 1, a chloroform solution of a compound represented by the following structural formula was applied to form a film of 20 nm in thickness by a spin-coating method, resulting in the hole transport layer 5.

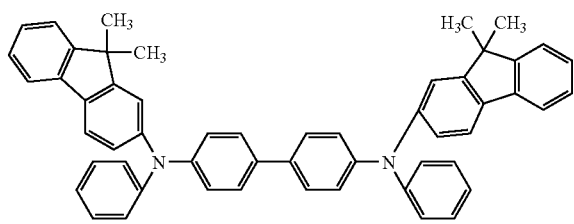

Furthermore, the fluorene compound represented as an exemplified compound No. 20 and a compound represented by the following structural formula (weight ratio of 100:5) were deposited into a film with a thickness of 20 nm by a vacuum evaporation method to form the luminescent layer 3. The film formation was performed under the conditions that the degree of vacuum at the time of evaporation was $1.0 \times 10^{-4}$ Pa and the film formation rate was 0.2 to 0.3 nm/sec.

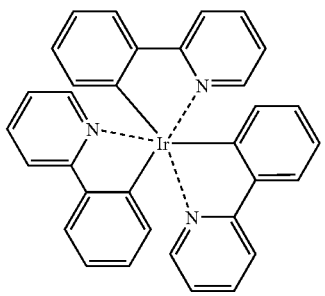

Furthermore, bathophenanthroline (BPhen) is deposited into a film of 40 nm in thickness by a vacuum evaporation method, resulting in the electron transport layer 6. The film formation was performed under the conditions that the degree of vacuum at the time of evaporation was $1.0 \times 10^{-4}$ Pa and the film formation rate was 0.2 to 0.3 nm/sec.

Next, after forming the cathode 4 in the same manner as in Example 1, the resultant structure was sealed. When a direct current voltage of 8 V was applied on the device thus obtained with an ITO electrode (anode 2) provided as a positive electrode and an Al—Li electrode (cathode 4) provided as a negative electrode, electric current was caused to flow into the device at a current density of 10.0 mA/cm$^2$ and green-colored luminescence at a luminance of 11000 cd/m$^2$ was observed.

Furthermore, when the current density was kept at 7.0 mA/cm$^2$ and the voltage was applied for 100 hours, the deterioration of luminance was small; an initial luminance of 8000 cd/m$^2$ was reduced to a luminance of 6500 cd/m$^2$ after 100 hours.

EXAMPLES 79 TO 87

Devices were prepared and evaluated in the same way as that of Example 78, except that a compound shown in Table 6 was used in place of the exemplified compound No. 20. The results are shown in Table 6.

Comparative Examples 10 to 12

Devices were prepared and evaluated in the same way as that of Example 78, except that the comparative compounds No. 1 to No. 3 were used in place of the exemplified compound No. 20. The results are shown in Table 6.

TABLE 6

| Example No. | Exemplified compound No. | Initial stage | | Durability | | |
|---|---|---|---|---|---|---|
| | | Applied voltage (V) | Luminance (cd/m$^2$) | Current density (mA/cm$^2$) | Initial luminance (cd/m$^2$) | Luminance after 100-hour (cd/m$^2$) |
| Example 78 | 20 | 8 | 11000 | 7.0 | 8000 | 6500 |
| Example 79 | 21 | 8 | 7000 | 7.0 | 6000 | 5000 |
| Example 80 | 23 | 8 | 10000 | 7.0 | 8000 | 7000 |
| Example 81 | 24 | 8 | 9500 | 7.0 | 7000 | 5500 |
| Example 82 | 25 | 8 | 12000 | 7.0 | 9500 | 7000 |
| Example 83 | 27 | 8 | 10000 | 7.0 | 7500 | 6500 |
| Example 84 | 32 | 8 | 8000 | 7.0 | 6000 | 5000 |
| Example 85 | 34 | 8 | 7000 | 7.0 | 6000 | 4500 |
| Example 86 | 36 | 8 | 7500 | 7.0 | 7000 | 5500 |
| Example 87 | 39 | 8 | 9000 | 7.0 | 8000 | 6500 |
| Comparative Example 10 | Comparative 1 | 8 | 3000 | 7.0 | 2000 | 800 |
| Comparative Example 11 | Comparative 2 | 8 | 1000 | 7.0 | 800 | 300 |
| Comparative Example 12 | Comparative 3 | 8 | 2000 | 7.0 | 1500 | 700 |

EXAMPLE 88

A device having the structure shown in FIG. 1 was prepared.

On a transparent conductive support substrate which was similar to that of Example 1, a solution prepared by dissolving 0.050 g of a fluorene compound represented as the exemplified compound No. 1 and 1.00 g of poly-N-vinyl carbazole (weight average molecular weight=63,000) in 80 ml of chloroform was applied to form a film of 120 nm in thickness by a spin-coating method (rotation speed=2000 rpm) to form the organic layer (luminescent layer 3).

Next, after forming the cathode 4 in the same manner as in Example 1, the resultant structure was sealed. When a direct current voltage of 10 V was applied on the device thus obtained with an ITO electrode (anode 2) provided as a positive electrode and an Al—Li electrode (cathode 4) provided as a negative electrode, electric the current was caused to flow into the device at a current density of 8.5 mA/cm$^2$ and blue-colored luminescence at a luminance of 3200 cd/m$^2$ was observed.

Furthermore, when the current density was kept at 5.0 mA/cm$^2$ and the voltage was applied for 100 hours in the nitrogen atmosphere, the deterioration of luminance was small; the initial luminance of 2500 cd/m$^2$ was reduced to a luminance of 2100 cd/m$^2$ after 100 hours.

EXAMPLES 89 TO 92

Devices were prepared and evaluated in the same way as that of Example 88, except that a compound shown in Table 7 was used in place of the exemplified compound No. 1. The results are shown in Table 7.

Comparative Examples 13 to 15

Devices were prepared and evaluated in the same way as that of Example 88, except that the comparative compounds No. 1 to No. 3 were used in place of the exemplified compound No. 1. The results are shown in Table 7.

TABLE 7

| Example No. | Exemplified compound No. | Initial stage | | Durability | | |
|---|---|---|---|---|---|---|
| | | Applied voltage (V) | Luminance (cd/m$^2$) | Current density (mA/cm$^2$) | Initial luminance (cd/m$^2$) | Luminance after 100-hour (cd/m$^2$) |
| Example 88 | 1 | 10 | 3200 | 5.0 | 2500 | 2100 |
| Example 89 | 6 | 10 | 3500 | 5.0 | 3000 | 2500 |
| Example 90 | 7 | 10 | 3400 | 5.0 | 2800 | 2500 |
| Example 91 | 15 | 10 | 2600 | 5.0 | 2200 | 1900 |
| Example 92 | 28 | 10 | 2200 | 5.0 | 2000 | 1800 |
| Comparative Example 13 | Comparative 1 | 10 | 850 | 5.0 | 750 | 400 |
| Comparative Example 14 | Comparative 2 | 10 | 650 | 5.0 | 600 | 80 |
| Comparative Example 15 | Comparative 3 | 10 | 800 | 5.0 | 700 | 250 |

As described above with reference to the embodiments and the examples, the organic luminescent device using the fluorene compound represented by the general formula [1] provides luminescence with a high luminance by the application of a low voltage and is excellent in durability. In particular, the organic layer containing the fused polycyclic compound of the present invention is excellent as the electron transport layer and is also excellent as the luminescent layer.

Furthermore, the device can be prepared by using a vacuum evaporation method or a casting method, so that the device having a large area can be easily prepared at a relatively low cost.

The invention claimed is:

1. A fluorene compound represented by the following general formula [I]:

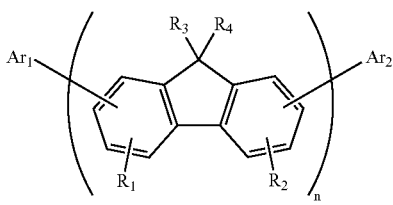

[I]

wherein $R_1$ and $R_2$ represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom, in which $R_1$ themselves or $R_2$ themselves which are bonded to different fluorene groups may be identical to or different from each other and $R_1$ and $R_2$ which are bonded to the same fluorene group may be identical to or different from each other;

wherein $R_3$ and $R_4$ represent a hydrogen atom, a substituted or unsubstituted alkyl group, a substituted or unsubstituted aralkyl group, a substituted or unsubstituted aryl group, or a substituted or unsubstituted heterocyclic group, in which $R_3$ themselves or $R_4$ themselves which are bonded to different fluorene groups may be identical to or different from each other and $R_3$ and $R_4$ which are bonded to the same fluorene group may be identical to or different from each other;

wherein $Ar_1$ and $Ar_2$ represent a substituted or unsubstituted fused polycyclic aromatic group represented by one of the following general formulae [II], [III] and [V] through [IX]

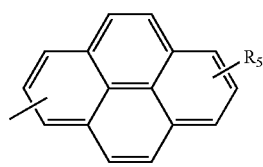

[II]

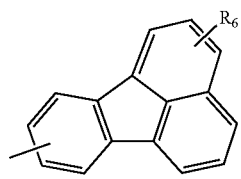

[III]

-continued

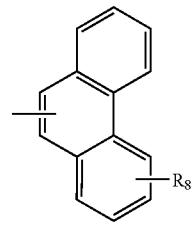

[V]

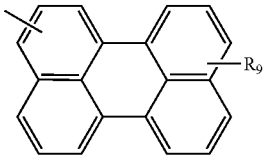

[VI]

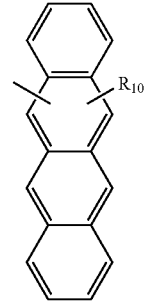

[VII]

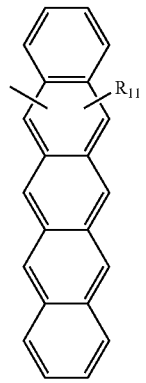

[VIII]

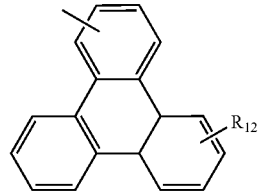

[IX]

wherein $R_5$, $R_6$ and $R_8$ to $R_{12}$ each represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom;

in which $Ar_1$ and $Ar_2$ may be identical to or different from each other; and wherein n represents an integer of 1 to 10.

2. The fluorene compound according to claim 1, wherein n is an integer of 1 to 3.

3. The fluorene compound according to claim 1, wherein the compound is represented by one of the following structural formulas:

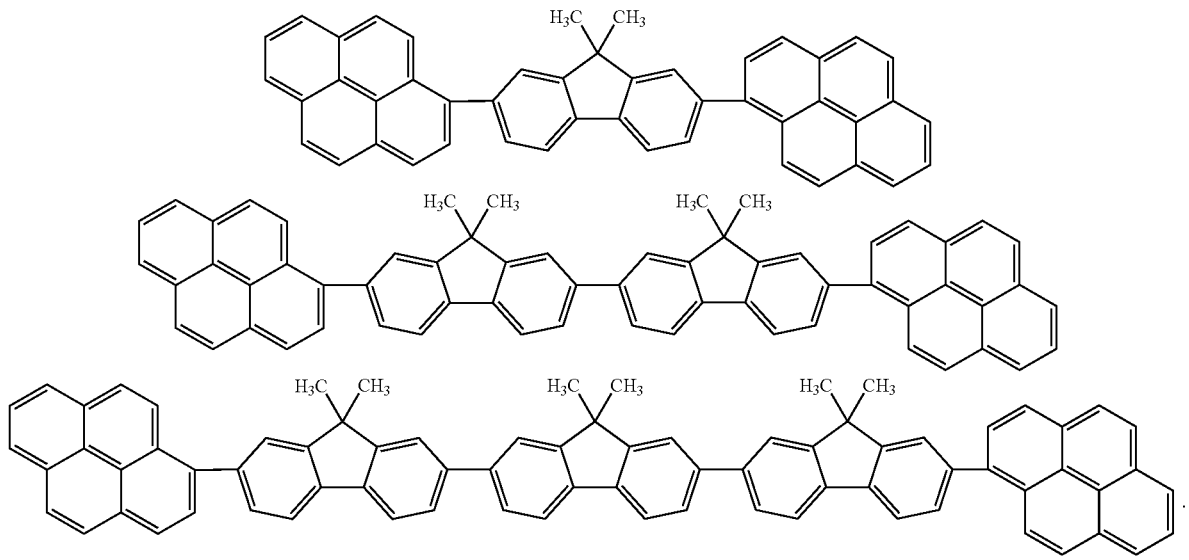

4. An organic luminescent device comprising at least a pair of electrodes including an anode and a cathode and one or a plurality of layers containing an organic compound sandwiched between the pair of electrodes, wherein at least one of the layers containing the organic compound contains at least one fluorene compound according to claim 1.

5. The organic luminescent device according to claim 4, wherein at least an electron transport layer or a luminescent layer among the layers containing an organic compound contains the at least one fluorene compound.

6. The organic luminescent device according to claim 4, wherein at least a luminescent layer among the layers containing an organic compound contains the at least one fluorene compound and an arylamine compound represented by the following general formula [X]:

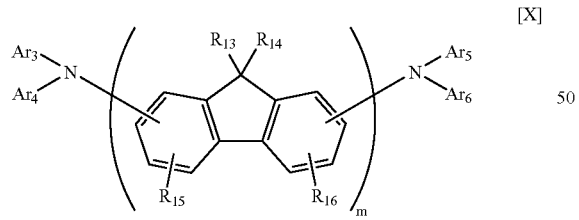

[X]

wherein $R_{13}$ and $R_{14}$ represent a hydrogen atom, a substituted or unsubstituted alkyl group, a substituted or unsubstituted aralkyl group, a substituted or unsubstituted aryl group, or a substituted or unsubstituted heterocyclic group, in which $R_{13}$ themselves or $R_{14}$ themselves which are bonded to different fluorene groups may be identical to or different from each other and $R_{13}$ and $R_{14}$ which are bonded to the same fluorene group may be identical to or different from each other;

wherein $R_{15}$ and $R_{16}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, in which $R_{15}$ themselves or $R_{16}$ themselves which are bonded to different fluorene groups may be identical to or different from each other and $R_{15}$ and $R_{16}$ which are bonded to the same fluorene group may be identical to or different from each other;

wherein $Ar_3$, $Ar_4$, $Ar_5$, and $Ar_6$ represent a substituted or unsubstituted aromatic group, a substituted or unsubstituted heterocyclic group, a substituted or unsubstituted fused polycyclic aromatic group, or a substituted or unsubstituted fused polycyclic heterocyclic group, in which $Ar_3$, $Ar_4$, $Ar_5$, and $Ar_6$ may be identical to or different from one another and $Ar_3$, $Ar_4$, $Ar_5$, and $Ar_6$ may be bonded with one another to form a ring; and wherein m represents an integer of 1 to 10.

7. The organic luminescent device according to claim 4, wherein at least a luminescent layer among the layers containing an organic compound contains the at least one fluorene compound and an arylamine compound represented by the following general formula [XI]:

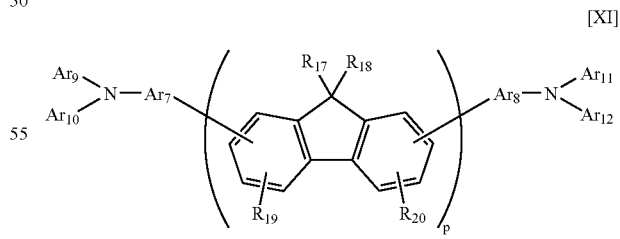

[XI]

wherein $R_{17}$ and $R_{18}$ represent a hydrogen atom, a substituted or unsubstituted alkyl group, a substituted or unsubstituted aralkyl group, a substituted or unsubstituted aryl group, or a substituted or unsubstituted heterocyclic group, in which $R_{17}$ themselves or $R_{18}$ themselves which are bonded to different fluorene groups may be identical to or different from each other and $R_{17}$ and $R_{18}$ which are bonded to the same fluorene group may be identical to or different from each other;

wherein $R_{19}$ and $R_{20}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, in which $R_{19}$ themselves or $R_{20}$ themselves which are bonded to different fluorene groups may be identical to or different from each other and $R_{19}$ and $R_{20}$ which are bonded to the same fluorene group may be identical to or different from each other;

wherein $Ar_7$ and $Ar_8$ represent a divalent substituted or unsubstituted aromatic group or a substituted or unsubstituted heterocyclic group, in which $Ar_7$ and $Ar_8$ may be identical to or different from each other;

wherein $Ar_9$, $Ar_{10}$, $Ar_{11}$, and $Ar_{12}$ represent a substituted or unsubstituted aromatic group, a substituted or unsubstituted heterocyclic group, a substituted or unsubstituted fused polycyclic aromatic group, or a substituted or unsubstituted fused polycyclic heterocyclic group, in which $Ar_9$ $Ar_{10}$, $Ar_{11}$, and $Ar_{12}$ maybe identical to or different from one another and $Ar_9$, $Ar_{10}$, $Ar_{11}$, and $Ar_{12}$ may be bonded with one another to form a ring; and wherein p represents an integer of 1 to 10.

8. The organic luminescent device according to claim 4, wherein at least a luminescent layer among the layers containing an organic compound contains the at least one fluorene compound and an arylamine compound represented by the following general formula [XII]:

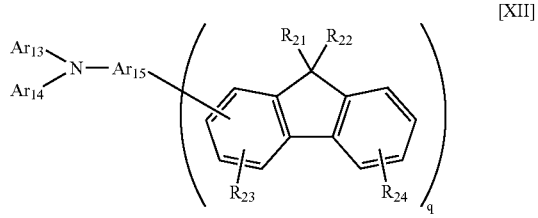

[XII]

wherein $R_{21}$ and $R_{22}$ represent a hydrogen atom, a substituted or unsubstituted alkyl group, a substituted or unsubstituted aralkyl group, a substituted or unsubstituted aryl group, or a substituted or unsubstituted heterocyclic group, in which $R_{21}$ themselves or $R_{22}$ themselves which are bonded to different fluorene groups may be identical to or different from each other and $R_{21}$ and $R_{22}$ which are bonded to the same fluorene group may be identical to or different from each other;

wherein $R_{23}$ and $R_{24}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, in which $R_{23}$ themselves or $R_{24}$ themselves which are bonded to different fluorene groups may be identical to or different from each other and $R_{23}$ and $R_{24}$ which are bonded to the same fluorene group may be identical to or different from each other;

wherein $Ar_{13}$ and $Ar_{14}$ represent a substituted or unsubstituted aromatic group, a substituted or unsubstituted heterocyclic group, a substituted or unsubstituted fused polycyclic aromatic group, or a substituted or unsubstituted fused polycyclic heterocyclic group, in which $Ar_{13}$ and $Ar_{14}$ may be identical to or different from each other and $Ar_{13}$ and $Ar_{14}$ may be bonded to each other to form a ring;

wherein $Ar_{15}$ represents a divalent substituted or unsubstituted aromatic group or a substituted or unsubstituted heterocyclic group; and wherein q represents an integer of 1 to 10.

9. The organic luminescent device according to claim 4, wherein at least a luminescent layer among the layers containing an organic compound contains the at least one fluorene compound and an arylamine compound represented by the following general formula [XIII]:

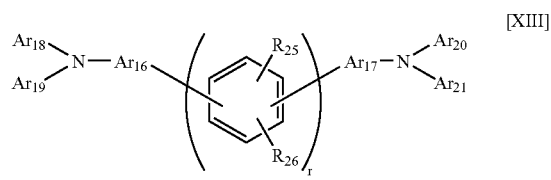

[XIII]

wherein $R_{25}$ and $R_{26}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, in which $R_{25}$ themselves or $R_{26}$ themselves which are bonded to different phenylene groups may be identical to or different from each other and $R_{25}$ and $R_{26}$ which are bonded to the same phenylene group may be identical to or different from each other;

wherein $Ar_{16}$ and $Ar_{17}$ represent a divalent substituted or unsubstituted aromatic group or a substituted or unsubstituted heterocyclic group, in which $Ar_{16}$ and $Ar_{17}$ may be identical to or different from each other;

wherein $Ar_{18}$, $Ar_{19}$, $Ar_{20}$, and $Ar_{21}$ represent a substituted or unsubstituted aromatic group, a substituted or unsubstituted heterocyclic group, a substituted or unsubstituted fused polycyclic aromatic group, or a substituted or unsubstituted fused polycyclic heterocyclic group, in which $Ar_{18}$, $Ar_{19}$, $Ar_{20}$, and $Ar_{21}$ may be identical to or different from one another and $AR_{18}$, $AR_{19}$, $Ar_{20}$, and $Ar_{21}$ may be bonded with one another to form a ring; and wherein r represents an integer of 1 to 10.

10. The organic luminescent device according to claim 4, wherein at least a luminescent layer among the layers containing an organic compound contains the at least one fluorene compound and an arylamine compound represented by the following general formula [XIV]:

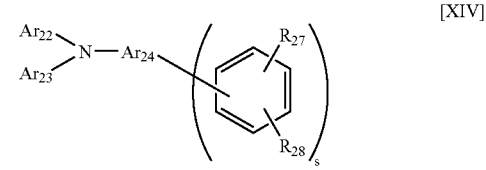

[XIV]

wherein $R_{27}$ and $R_{28}$ represent a hydrogen atom, a substituted or unsubstituted alkyl group, a substituted or unsubstituted aralkyl group, a substituted or unsubstituted aryl group, a substituted or unsubstituted heterocyclic group, a cyano group, or a halogen atom, in which $R_{27}$ themselves or $R_{28}$ themselves which are bonded to different phenylene groups may be identical to or different from each other and $R_{27}$ and $R_{28}$ which are bonded to the same phenylene group may be identical to or different from each other;

wherein $Ar_{22}$ and $Ar_{23}$ represent a substituted or unsubstituted aromatic group, a substituted or unsubstituted heterocyclic group, a substituted or unsubstituted fused polycyclic aromatic group, or a substituted or unsubstituted fused polycyclic heterocyclic group, in which $Ar_{22}$ and $Ar_{23}$ may be identical to or different from each other and $Ar_{22}$ and $Ar_{23}$ may be bonded to each other to form a ring;

wherein $Ar_{24}$ represents a divalent substituted or unsubstituted aromatic group or a substituted or unsubstituted heterocyclic group; and wherein s represents an integer of 1 to 10.

11. The organic luminescent device according to claim 4, wherein at least a luminescent layer among the layers containing an organic compound contains the at least one fluorene compound and an acetylene compound represented by the following general formula [XV]:

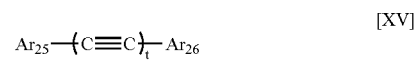

wherein $Ar_{25}$ and $Ar_{26}$ represent a substituted or unsubstituted aromatic group, a substituted or unsubstituted heterocyclic group, a substituted or unsubstituted fused polycyclic aromatic group, or a substituted or unsubstituted fused polycyclic heterocyclic group, in which $Ar_{25}$ and $Ar_{26}$ may be identical to or different from each other; and wherein t represents an integer of 1 to 5.

* * * * *

UNITED STATES PATENT AND TRADEMARK OFFICE
CERTIFICATE OF CORRECTION

PATENT NO. : 7,241,513 B2
APPLICATION NO. : 10/491745
DATED : July 10, 2007
INVENTOR(S) : Koichi Suzuki et al.

It is certified that error appears in the above-identified patent and that said Letters Patent is hereby corrected as shown below:

ON COVER PAGE AT (56) OTHER PUBLICATIONS

After "C.W. Tang, et al.,": "pp. 913-915." should read --pp. 913-915 (1987)--.

COLUMN 13

Ex. 27, " 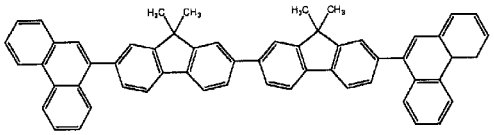 " should read

-- 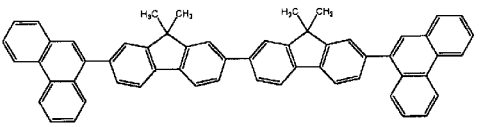 --; and

Ex. 31, " 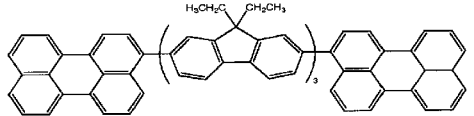 " should read

-- 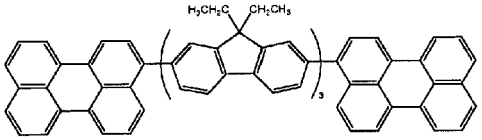 --.

UNITED STATES PATENT AND TRADEMARK OFFICE
CERTIFICATE OF CORRECTION

PATENT NO. : 7,241,513 B2  Page 2 of 4
APPLICATION NO. : 10/491745
DATED : July 10, 2007
INVENTOR(S) : Koichi Suzuki et al.

It is certified that error appears in the above-identified patent and that said Letters Patent is hereby corrected as shown below:

COLUMN 25

Ex. AA-28, " 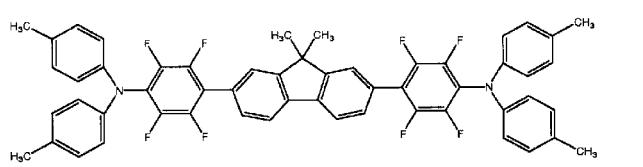 "

should read

-- 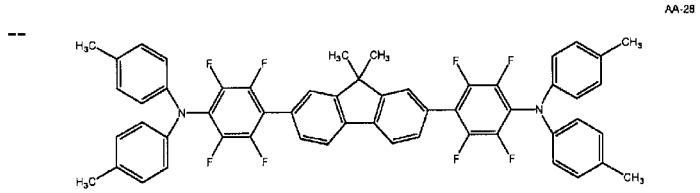

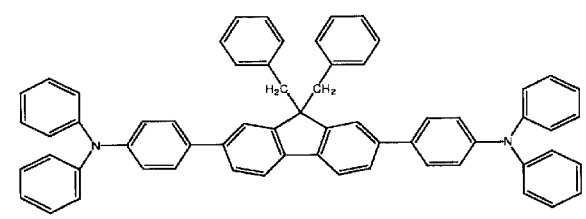 --.

COLUMN 26

Ex. AA-25, " 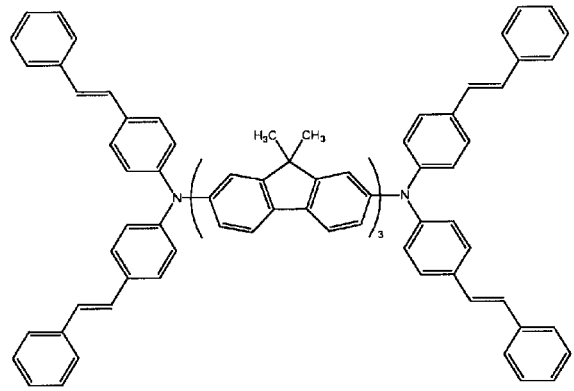 "

UNITED STATES PATENT AND TRADEMARK OFFICE
CERTIFICATE OF CORRECTION

PATENT NO. : 7,241,513 B2  Page 3 of 4
APPLICATION NO. : 10/491745
DATED : July 10, 2007
INVENTOR(S) : Koichi Suzuki et al.

It is certified that error appears in the above-identified patent and that said Letters Patent is hereby corrected as shown below:

should read

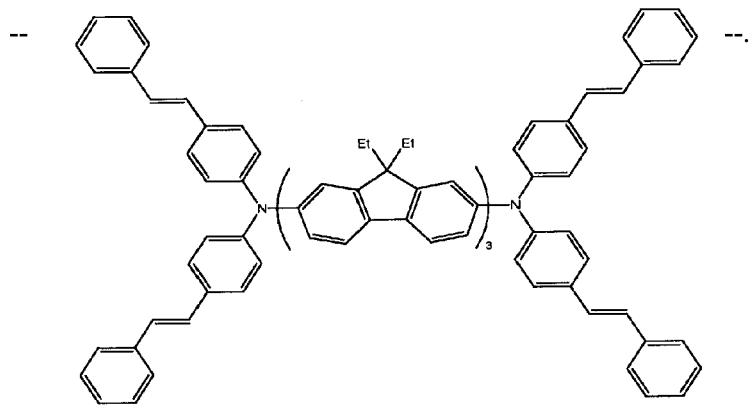

COLUMN 35

Ex. AA-58, " 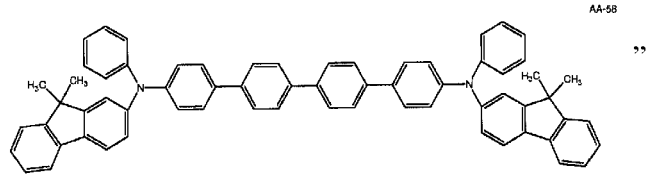 "

should read

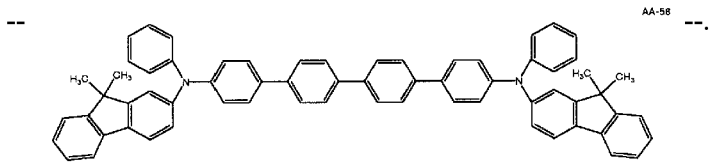

COLUMN 55

Line 22, "NaCO₃ aq." should read --Na₂CO₃ aq.--.

UNITED STATES PATENT AND TRADEMARK OFFICE
CERTIFICATE OF CORRECTION

PATENT NO.         : 7,241,513 B2
APPLICATION NO. : 10/491745
DATED                 : July 10, 2007
INVENTOR(S)       : Koichi Suzuki et al.

It is certified that error appears in the above-identified patent and that said Letters Patent is hereby corrected as shown below:

COLUMN 56

Lines 31-39, " 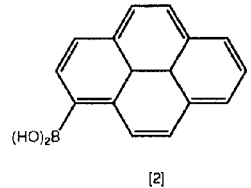 " should read

-- 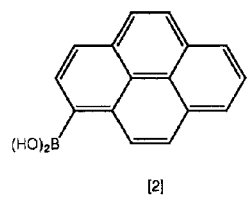 --.

COLUMN 75

Line 22, "maybe" should read --may be --.

COLUMN 76

Line 43, "$AR_{18}$, $AR_{19}$," should read --$Ar_{18}$, $Ar_{19}$,--.

Signed and Sealed this

Twenty-seventh Day of May, 2008

JON W. DUDAS
*Director of the United States Patent and Trademark Office*